United States Patent [19]

Yang et al.

[11] Patent Number: 4,856,528

[45] Date of Patent: Aug. 15, 1989

[54] TUMOR VOLUME DETERMINATION

[75] Inventors: Nai-Chuen Yang, Baltimore; Peter K. Leichner, Cockeysville, both of Md.

[73] Assignee: John Hopkins University, Baltimore, Md.

[21] Appl. No.: 66,554

[22] Filed: Jun. 26, 1987

[51] Int. Cl.[4] .............................................. A61B 6/03
[52] U.S. Cl. ...................................... 128/653; 382/6; 382/18; 382/22
[58] Field of Search ....................... 364/414, 415, 564; 378/901; 382/6, 18, 22; 128/653, 659; 358/111

[56] References Cited

U.S. PATENT DOCUMENTS

| | | | |
|---|---|---|---|
| 3,705,383 | 12/1972 | Frayer | 382/18 |
| 4,361,830 | 11/1982 | Honma et al. | 382/22 |
| 4,538,227 | 8/1985 | Toraichi et al. | 364/414 |
| 4,538,299 | 8/1985 | DeForest | 382/6 X |
| 4,590,558 | 5/1986 | Glover et al. | 364/414 |
| 4,606,065 | 8/1986 | Beg et al. | 382/18 |

OTHER PUBLICATIONS

Cassell et al., "Automatic Outlining Technique for EMI Scanner Pictures", Med. & Biol. Eng. & Comput., 1979, vol. 17, No. 5, pp. 693–694.
Cancer Drug Delivery, vol. 1, No. 4, 1984—Comparative Tumor Dose from 131 I-Labeled Polyclonal Anti--Ferritin . . . by Peter K. Leichner et al.
Radiation Oncology Biology Physics, Mar. 1981, vol. 7, No. 3, Dosimetry of 131-I-Labeled Anti–Ferritin in Hepatoma: A Model for Radioimmunoglobulin—Peter K. Leichner et al.
Cancer Treatment Reports—vol. 67, Nos. 7–8, Jul.-/Aug. 1983—Dosimetry of 131 I-Labeled Anti–Ferritin in Hepatoma: Specific Activities in the Tumor and Liver—Peter K. Leichner et al.
Radiology, May 1983—pp. 495–497—Work in Progress: Serial Evaluation of Tumor Volume Using Computed Tomography and Contrast Kinetics[1], David A. Oppenheimer et al.
Computerized Tomography, vol. 4, pp. 55 to 65—On the Impact of CT Scanning on Radiotherapy Planning—J. Van Dyk et al.
Radiology 141:525-527, Nov. 1981—Measurement of Liver and Spleen Volume by Computed Tomography—J. Michael Henderson.
J. Comput. Assist Tomogr., vol. 5, No. 1, 1981—Determination of Liver, Kidney, and Spleen Volumes by Computed Tomography-Moss et al.
J. Comput. Assist Tomogr., vol. 5, No. 5, 1981—Volumetric CT Analysis of Hepatic Tumors—Moss et al.
Feb. 1979—Annals of Internal Medicine, vol. 90, No. 2—Accurate Measurement of Liver, Kidney and Spleen Volume and Mass by Computerized Axial Tomography—Heymsfield et al.
AJR:138, Feb. 1982—pp. 329-333—Volume Determinations Using Computed Tomography—Richard S. Breiman et al.

Primary Examiner—Ruth S. Smith
Attorney, Agent, or Firm—Cushman, Darby & Cushman

[57] ABSTRACT

A computer-implemented arrangement (apparatus and method) for semi-automatically determining from CT image data the volume of a tumor. A primary application is to determining a tumor volume for patients with hepatoma and primary hepatic cholangiocarcinoma. CT image data of a scanned organ, stored on a magnetic tape, is read into a computer. This data includes for each of plural slices of predetermined thickness a plurality of pixels defining the slice and a CT number representing tissue density corresponding to each pixel. An image of the first slice is displayed on a monitor. A region of interest (ROI) approximating an outline of the organ is automatically generated, which outline is visually modified, if necessary, by an operator to closely correspond to the organ's outline. The particular pixels within the organ's outline and the CT numbers associated therewith are stored as a local histogram of the slice, the local histogram including data indicative of the number of pixels within the organ's outline having each unique CT number. Local histograms, produced in a similar manner for each slice, are summed to generate a global histogram indicative of the number of pixels within the organ outline's of respective slices having each unique CT number. From the global histogram, a demarcation CT number distinguishing tumor tissue from normal organ tissue is determined. From the global histogram and demarcation CT number, the organ volume and tumor volume are determined.

10 Claims, 10 Drawing Sheets

TUMOR VOLUME DETERMINATION

BACKGROUND OF THE INVENTION

This invention relates in general to the radiological arts. More specifically, it provides a semi-automated process for determining the volume of a tumor within a body organ. The invention has particular application to cancer treatment programs and research.

With the now widespread use of CT scanners, it has become increasingly recognized that rapid and accurate organ and tumor volume determinations from Computed Tomography (CT) image data can be of great value in radiotherapy treatment planning. See for example, the following publications - Hobday P, Hodson NJ, Husband J, Parker RP, MacDonald JS, "Computed tomography applied to radiotherapy treatment planning: techniques and results" Radiology 1979; 133:477-82; and Van Dyk J, Battista JJ, Cunningham JR, Rider WD, Sontag MR, "On the impact of CT scanning on radiotherapy planning" Comput Tomogr 1980; 4:55-65. Tumor volume determinations are also important for radiation dose estimates for normal and tumor issues in radiolabeled antibody cancer therapy. See for example the following publications - Leichner PK, Klein JL, Garrison JB, et al "Dosimetry of $^{131}$I-labeled antiferritin in hepatoma: a model for radioimmunoglobulin dosimetry" Int J Radiat Oncol Biol Phys 1981;7:323-33; Leichner PK, Klein JL, Siegelman SS, Ettinger DS, Order SE "Dosimetry of 131I-labeled antiferritin in hepatoma: specific activities in the tumor and liver" Cancer Treat Rep 1983;67:647-58; and Leichner PK, Klein JL, Fishman EK, Siegelman SS, Ettinger DS, Order SE "Comparative tumor dose from $^{131}$I-labeled polyclonal anti-ferritin, anti-AFP, and anti-CEA in primary liver cancers" Cancer Drug Delivery 1984; 1:321-8. Such volume determinations are also important for the assessment of tumor response to new treatment modalities. See for example the following publication—Order SE, Klein JL, Leichner PK, et al, "Radiolabeled antibodies in the treatment of primary liver malignancies" In:Levin B, Riddell R, eds. Gastrointestinal cancer, New York: Elsevier-North Holland, 1984;222-32.

Volume computations from CT have been investigated by several authors using a variety of methods. For example, see the following publications—Heymsfield SB, Fulenwider T, Nordinger B, Barlow R, Sones P, Kutner M. "Accurate measurement of liver kidney, and spleen volume and mass by computerized axial tomography" Ann Intern Med 1979;90:185-7; Henderson JM, Heysfield SB, Horowitz J, Kutner MH, "Measurement of liver and spleen volume by computed tomography" Radiology 1981; 141:525-7; Moss AA, Cann CE, Friedman MA, Marcus FS, Resser KJ, Berninger W., "Volumetric CT analysis of hepatic tumors" J Comput Assist Tomogr 1981;5:714-8; Moss AA, Friedman MA, Brito AC, "Determination of liver, kidney, and spleen volumes by computed tomography: an experimental study in dogs" J Comput Assist Tomogr 1981; 5:12-4; Breiman RS, Beck JW, Korobkin M, et al, "Volume determinations using computed tomography. AJR 1982; 138:329-33; Oppenheimer DA, Young SW, Marmor JB, "Work in progress, serial evaluation of tumor volume using computed tomography and contrast kinetics" Radiology 1983; 147:495-7; Reid MH, "Organ and lesion volume measurements with computed tomography" J Comput Assist Tomogr 1983;7:268-73.

Moss et al [Moss AA, Cann CE, Friedman MA, Marcus FS, Resser KJ, Berninger W., "Volumetric CT analysis of hepatic tumors" J Comput Assist Tomogr 1981;5:714-8] have described a computer program for calculating the mean CT number of normal liver tissue in each CT "slice" and obtaining total liver volume by summing over all CT slices containing liver. Tumor volume in each slice was obtained by subtracting a Gaussian distribution of CT numbers for normal liver from the bimodal CT number distribution for the whole liver. The results from all slices were summed to obtain partial tumor and liver volumes for each patient.

It is known to determine tumor and liver volumes from sets of manually contoured CT slices. However, as practiced in the prior art, such determinations are time-consuming and labor-intensive. A radiologist must outline with a grease pencil regions of interest (ROI) corresponding to tumor and normal liver on patients' CT films. These contours are then digitized, the areas computed by numerical integration, and multiplied by slice thickness to obtain tumor and normal liver volumes for each slice. Total volume is obtained by summing over all slices. In spite of the fact that such methodology is extremely cumbersome, it was carried out for several years (1979-1984), and clinically relevant and important results were obtained and published in scholarly journals. The method of Moss et al also required manual contouring, directly on a video monitor, and slice-by-slice analysis of patients' CT scans.

To handle the increased number of patients due to expansion of the radiolabeled antibody treatment programs, it became evident that further automation was required to provide clinicians with timely information about tumor response to therapy and for radiolabeled antibody treatment planning.

SUMMARY OF THE INVENTION

The technique for determining the volume of a tumor within a body organ presented herein is more automated than prior art methods. The claimed method has several advantages over known methodologies. Regions of interest corresponding to tumor and normal liver are generated in a computer-assisted manner which does not require the presence of a trained radiologist. Secondly, the decision as to tumor and normal liver tissues within the regions of interest is based on a global histogram method which includes all CT slices in a patient's scan. This is both computationally faster and statistically more reliable than previous methods.

The present invention provides a more automated technique for determining from CT image data the volume of a tumor within a body organ. The method can be summarized in "outline" form as follows:

CT image data previously collected for a plurality of contiguous organ slices is read.

An image of the first slice is displayed on a monitor.

An operator inputs upper and lower limit CT numbers to define a boundary condition of the organ.

The operator visually identifies a "seed" pixel that is clearly within the organ.

The computer generates and displays on the monitor, based on defining data input by the operator, a region of interest (ROI) corresponding to an outline of the organ.

If the computer-generated ROI is unsatisfactory, the operator visually modifies the computer generated approximate organ outline to produce a modified ROI that more accurately identifies the organ outline.

Once an accurate organ boundary has been visually established, the computer determines which pixels are within the boundary and stores as a local histogram of the slice, information identifying the number of pixels and CT number associated therewith.

This process is repeated for each slice to produce a local histogram of each slice.

The local histograms are summed to produce a global histogram indicative of the number of pixels within the respective organ boundaries of all slices having each unique CT number.

A demarcation CT number is determined that distinguishes between normal organ tissue and tumor. This may be done by the operator looking at the global histogram.

Based on the demarcation CT number and the global histogram, organ volume and tumor volume are computed.

DETAILED DESCRIPTION OF THE PREFERRED EMBODIMENT

Figure 1:
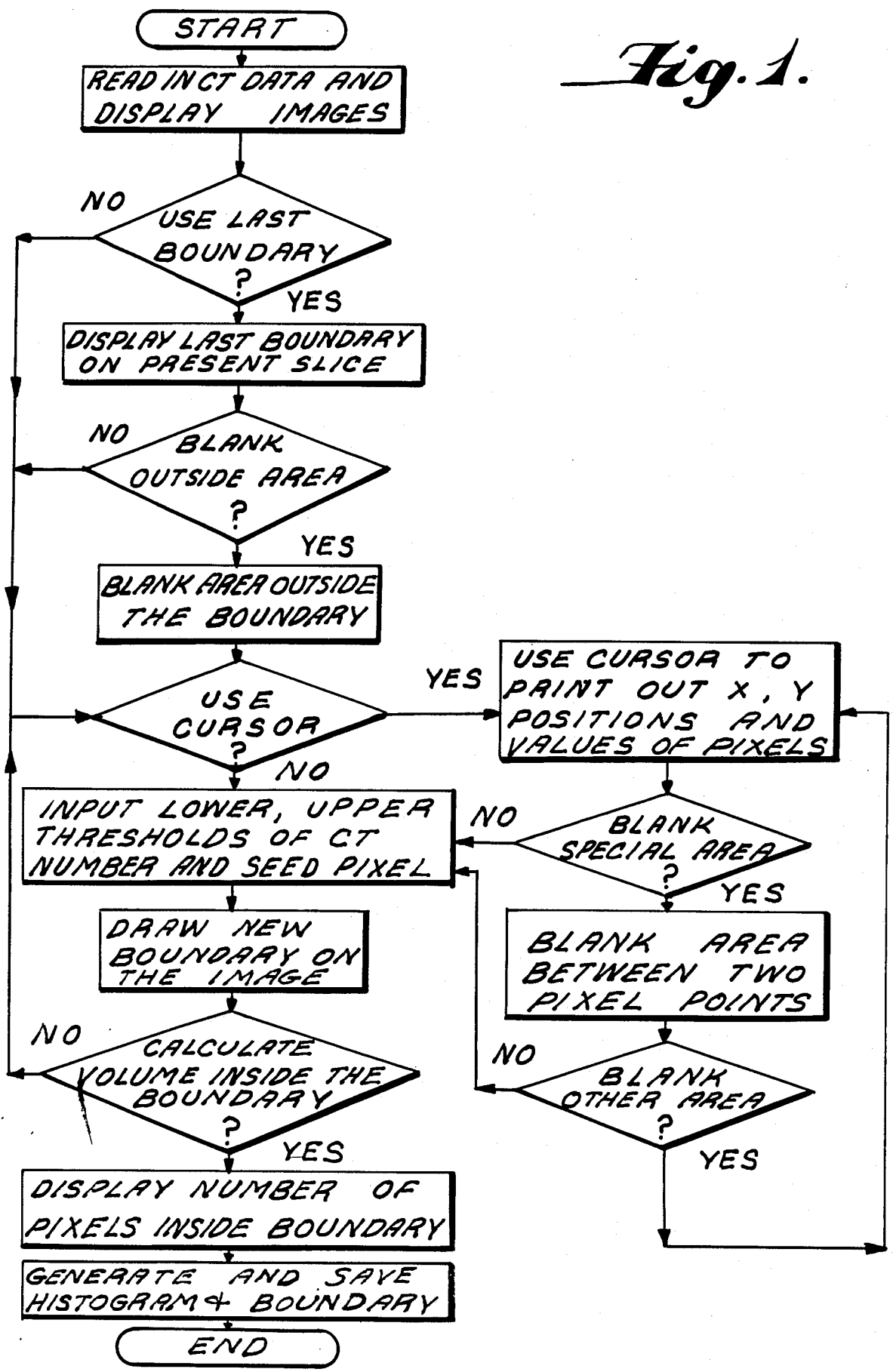
FIG. 1 is a general flow chart of the tumor volume determination method according to the present invention.
Figure 14:
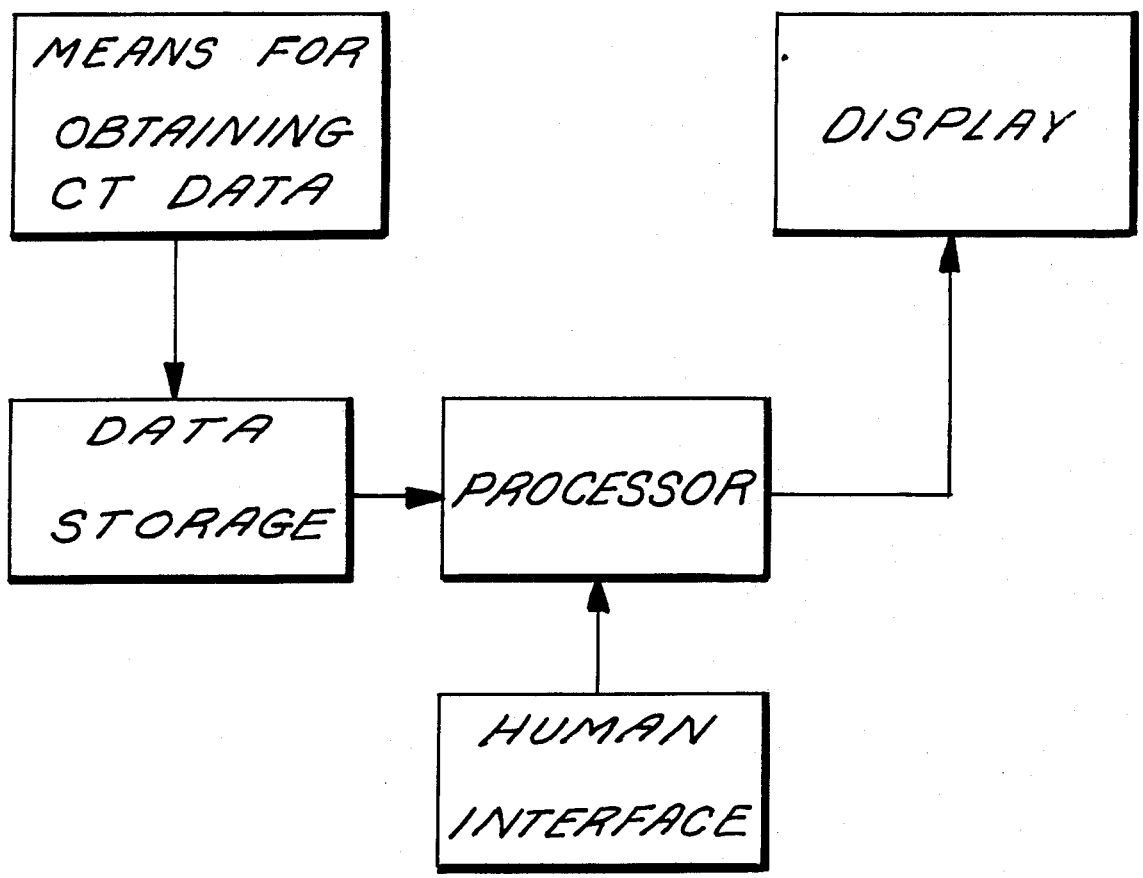
FIG. 14 is a block diagram of a computer arrangement for carrying out the method set forth in the FIG. 1 flow chart.

FIG. 1 is a general flow chart of the tumor volume determination technique according to the invention. A block diagram of a computer for carrying out the FIG. 1 method is shown in FIG. 14.

At step 100 CT image data, previously gathered by CT scanning the patient, is read and images of the CT "slices" are displayed. Usually CT image data collected by a CAT scan procedure is stored on a magnetic tape. Therefore, this step includes reading the CT image data from that magnetic tape, previously produced. The CT image data includes data for each of a plurality of contiguous slices of predetermined thickness of the tumor bearing organ. Preferably, the slices are 8 mm thick, but other slice thicknesses can be used. The CT image data includes a CT number representing tissue density for each of a plurality of pixels defining the slice.

Steps 100-128 are carried out for each slice (image). For a given slice an image of that slice is displayed. The operator is asked at step 102 whether the boundary for the previous slice is to be applied to the now displayed slice. Of course, if the operator is viewing the first slice of a series of slices, there is no prior boundary to use. If, at step 102, the operator answers "yes", program control proceeds to step 104 and the boundary of the previous slice is superimposed on the now displayed slice. This gives the operator a short cut starting point for identifying the organ's boundary in the slice now being displayed. In steps 106 and 108, the operator can set to zero all pixels for the now displayed slice that are outside the ROI carried over from the previous slice.

If the operator is viewing the first slice, or for some other reason does not want to start with the boundary from the previous slice, he answers "no" at step 102 and program control flows to step 110. At step 110, the operator is asked whether he wants to use the cursor. The cursor appears as a cross mark on the monitor and is under the control of a mouse. If the operator answers "yes", program control then proceeds to step 112. The operator can move the cursor, using the mouse, to any point on the image. The computer will provide the x and y position of the pixel and its CT number. The process at step 112 can help the operator determine lower and upper thresholds of CT numbers that he will have to specify at step 120.

If the operator has decided at step 110 not to use the cursor, he is asked to input lower and upper thresholds of CT numbers. These thresholds are used by the computer to look for boundary pixels. These are pixels at the edge of the tumor bearing organ. Using a "seed" pixel visually selected by the operator and the thresholds input at step 120, the computer automatically generates what it thinks is the boundary of the organ. To input the seed pixel, the operator moves the cursor to an arbitrary pixel that is clearly within the boundary of the organ, as it appears on the monitor. Beginning at the seed pixel, the computer searches in accordance with a predetermined routine from one pixel to the next until it locates a pixel meeting the threshold criteria input at step 120. The first pixel so located is considered to be the first boundary pixel. The nearest neighboring pixels to the first boundary pixel are examined to determine if any of them meet the threshold condition. Each such pixel located is also considered to be a boundary pixel. A vector is "drawn" from the first boundary pixel to the second boundary pixel, etc. This process continues from one pixel to the next until the entire boundary line of the organ has be drawn by the computer.

From step 122, program control proceeds to step 124 where the operator is asked whether he wants to calculate the area inside the now displayed boundary. If the operator is confident that the boundary now shown on the monitor is accurate, no adjustment is necessary and the operator can answer "yes" and proceed to step 126. However, if the boundary is not accurate, the operator must answer "no" and make a boundary correction. If the operator answers "no", program control then proceeds to step 110. The operator can use the cursor to adjust the boundary to be more accurate. This allows the operator to correct the boundary line for errors caused by tissues abutting the organ that have close CT numbers to the organ tissue. For example, in the case of a liver scan, the boundary line automatically generated by the computer often includes soft tissue between ribs. This boundary correction is carried out at steps 114–118. At step 114 where the operator is asked if he wants to blank a special area. If he answers "yes" program control then proceeds to step 116 where the operator can adjust the boundary generated by the computer. He does this by moving the cursor so as to identify two separate and distinct points on the true boundary (not the one generated by the computer). The computer than adjusts the boundary to include those points, thereby eliminating from within the boundary points that do not belong.

Only after the operator is satisfied with the boundary appearing on the monitor does he answer "yes" at step 124. Program control then moves to step 126. At step 126, the computer displays the number of pixels inside the boundary. At step 128, data is stored in the form of a local histogram for the slice then being displayed. The local histogram includes data indicative of the number of pixels having each particular CT number.

Steps 100–128 are repeated for each slice so that a local histogram of each slice is produced. The local histograms are summed to produce a global histogram indicative of the number of pixels within the organ boundaries of respective slices having each unique CT number. Then, there is determined from the global histogram a demarcation CT number that distinguishes between normal organ tissue and tumor. Depending upon the histogram, this is done in various ways. From the demarcation CT number and the global histogram, organ volume and tumor volume are computed.

The manner of determining the demarcation CT number and the determination of tumor and organ volumes will be further described in the following material related to a study. In part, the manner for determining automatically tumor volume from the global histogram depended upon determining some constants to be used in calculation empirically.

In a study of 56 patients with primary liver cancers it became evident that the distribution of CT numbers was not necessarily bimodal, and that a slice-by-slice determination of mean CT numbers did not provide sufficient statistical information to distinguish between normal and tumor bearing liver tissues. An algorithm was, therefore, developed to generate histograms of CT number distributions for all of the CT slices in patients' liver scans (global histograms) without having to determine the mean CT numbers corresponding to normal liver in individual slices. This provided more reliable statistical information and had the advantage of being computationally faster.

All patients in this study had histologically confirmed primary liver cancers, and CT examinations were performed using a Siemens Somatom DR3 body scanner. Livers were scanned at contiguous 8-mm intervals with an 8-mm slice thickness while patients suspended respiration at resting lung volume. Reconstructed transaxial slices were stored on magnetic tape in 256×256 matrices and analyzed on a minicomputer. Semiautomatic computer software, as described above, was used to define a region of interest (ROI) corresponding to the boundary of the whole liver in each slice, and a local histogram of the CT numbers within the ROI was generated. A global histogram was then obtained by summing over the local histograms for each slice. Total liver volume was computed from the number of pixels in the global histogram and the known pixel size and slice thickness of 8 mm.

Tumor volume computations were based on an analysis of global histograms. The global histograms fell into three categories. Some of the global histograms had three distinct peaks, some had two distinct peaks, and some had only a single peak. Quantitative information about liver and tumor volumes was extracted from these CT number distributions in a consistent manner by fitting them to a sum of three gaussian functions given by $$F(n) = \sum_{i=1}^{3} A_i \exp\left[ -\frac{(n - n_i)^2}{2\sigma_i^2} \right]. \tag{1}$$

In the above equation, n represented the CT numbers and $n_i$ their mean value for each of the gaussian functions; $A_i$ and $\sigma_i$ were the corresponding amplitude and variance, respectively.

Figure 2A:
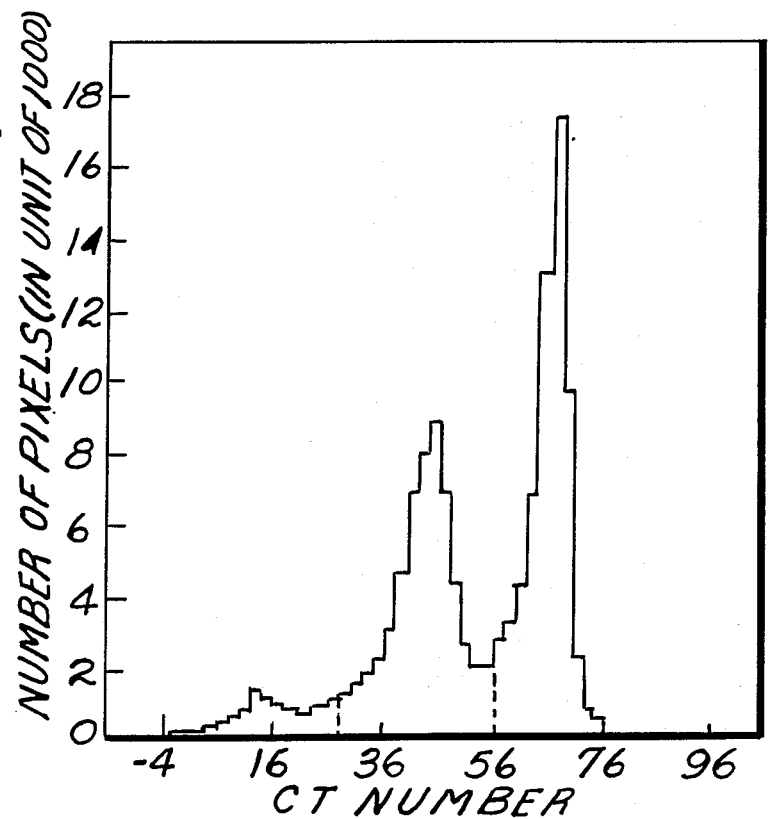
FIG. 2(i a) is a representative global histogram of a CT number distribution with three distinct peaks. Peaks 1 and 2 were associated with normal liver (NL) and tumor (T), respectively. The third peak was associated with necrotic tissue within the core of a hepatoma. The dashed lines were threshold CT numbers for normal liver and tumor.
FIG. 2(b) is the same histogram as in FIG. 2(a) with the three gaussian fitting functions superimposed on the histogram.
Figure 2B:
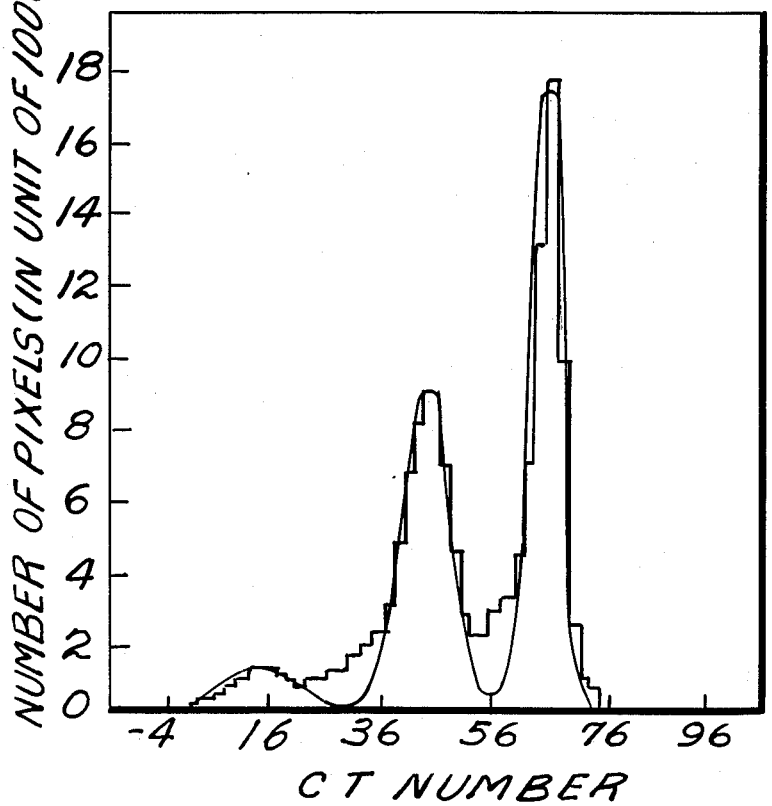

A representative CT number distribution with three distinct peaks is shown in FIG. 2(a), and the three gaussian fitting functions superimposed on the histogram are displayed in FIG. 2(b). The gaussian function with the largest amplitude and the highest mean CT number (peak no. 1) corresponded to normal liver (NL) and the gaussian function with the second-largest amplitude and lower mean CT number (peak no. 2) to tumor (T). By highlighting pixels in CRT displays of CT slices, it was determined that the third peak in FIGS. 2(a) and 2(b) was representative of tissue within the core of solid hepatomas. The mean value of CT numbers in the third peak was even lower than that of the tumor itself and indicated the presence of necrotic tissue.

The gaussian fitting functions also made it possible to define threshold CT numbers for tumor and liver tissues and to determine the probability for normal pixels to be representative of these tissues. For example, the dashed lines in FIG. 2(a) were located at CT numbers corresponding to the minima between gaussian functions 1 and 2 and gaussian functions 2 and 3 in FIG. 2(b), respectively. All pixels to the right of the dashed line between peaks 1 and 2 in FIG. 2(a) were interpreted as normal liver, and pixels falling between the two dashed lines as tumor. This interpretation was verified by highlighting these pixels in CT slices on CRT displays. From the gaussian fitting functions it followed that the probability for pixels within these two ranges of CT numbers to be representative of normal liver and tumor tissues was close to unity (>0.999). All pixels corresponding to tumor were summed in the global histograms, and tumor volumes were computed in the same manner as whole liver volumes.

Figure 3A:
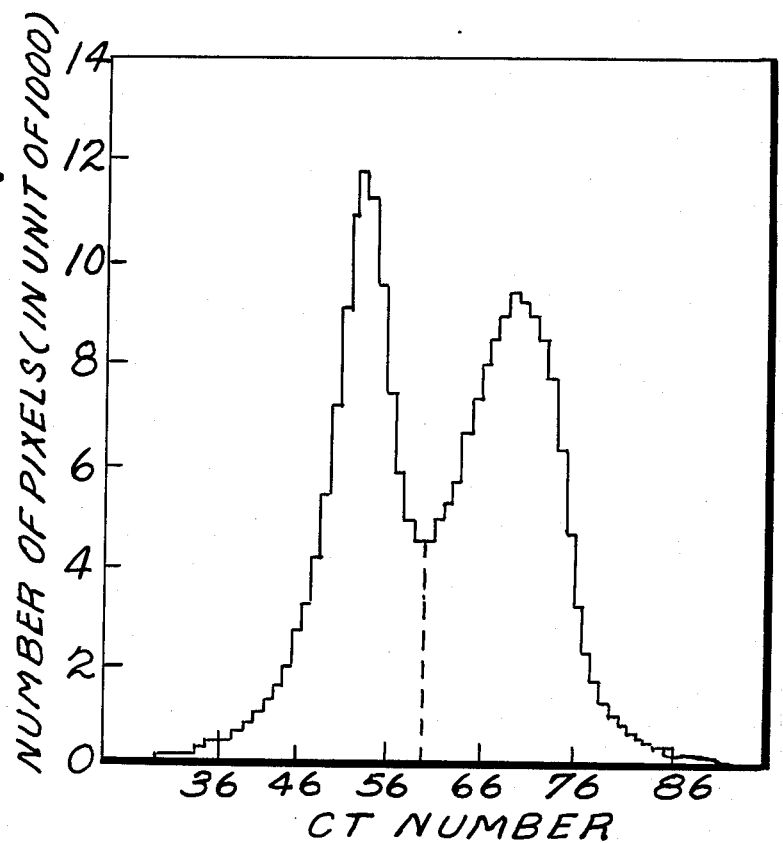
FIG. 3(a) is a representative global histogram with two distinct peaks.; Peak No. 1 was associated with normal liver (NL) and Peak No. 2 with tumor (T). The dashed line represents the threshold CT number for tumor and normal liver.
Figure 3B:
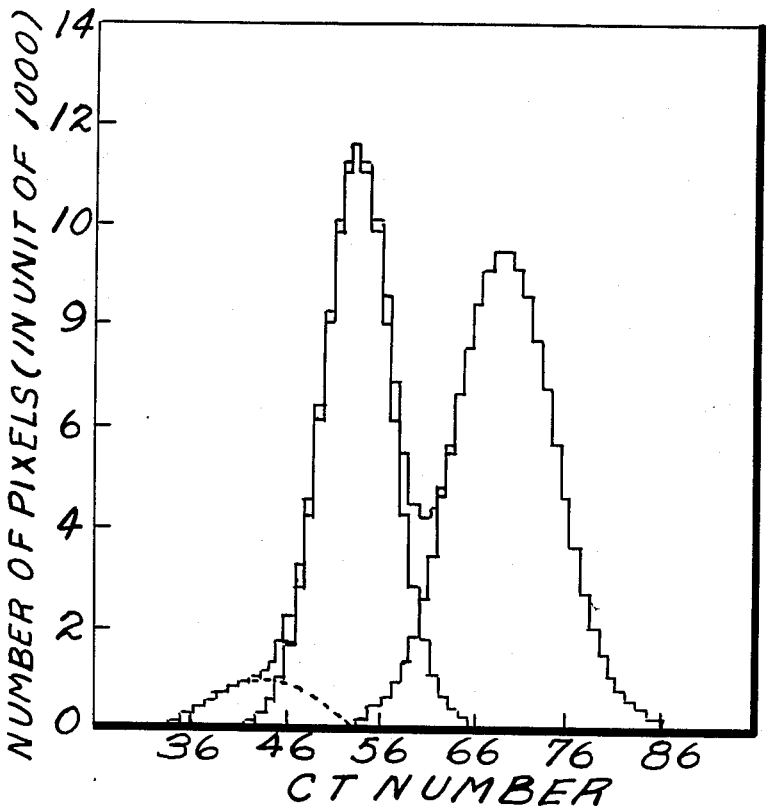
FIG. 3(b) is a global histogram (outside curve) for the same patient as in FIG. 3(a). The three gaussian functions were summed to get the global histogram. The gaussian function with the highest mean CT number corresponded to normal liver (NL), and the gaussian function with the largest amplitude and lower mean CT number to tumor (T).

A representative global histogram with two distinct peaks is shown in FIG. 3(a). FIG. 3(b) shows the three gaussian functions and the histogram fit resulting from the addition of these functions. The third gaussian function (dotted line) with the lowest amplitude was required to obtain a satisfactory fit to the asymmetric portion of the histogram in the range of the lowest CT numbers. Additionally, for CT numbers from 30 to 46 the third gaussian corresponded to low-density structures such as blood vessels, fatty tissue, and bile ducts. This was ascertained by highlighting pixels in this range of CT numbers. In the case of global histograms with only one or two peaks, the third gaussian did not reflect necrotic tissue because it extended over a range of CT numbers that was higher than that of the third gaussian in FIG. 2(b). As before, the gaussian function with the highest mean value of CT numbers was interpreted as representing normal liver (peak no. 1), and the gaussian fitting function for peak no. 2 as representing tumor. Threshold CT numbers for normal liver and tumor in these histograms corresponded to the minimum value of the gaussian fitting functions in the overlap region between peaks 1 and 2 in FIG. 3(b). The dashed line in FIG. 3(a) was obtained in this manner. All pixels with CT numbers above this threshold were counted as normal liver and all others as tumor. Pixels in these two ranges of CT numbers were highlighted in different colors on CRT displays of CT slices and identification of normal liver and tumor determined to be satisfactory by experienced observers. An analysis of the gaussian fitting functions showed that the probability for pixels to represent normal liver and tumor in each of the two CT number ranges was 0.960 and 0.942, respectively.

Figure 4:
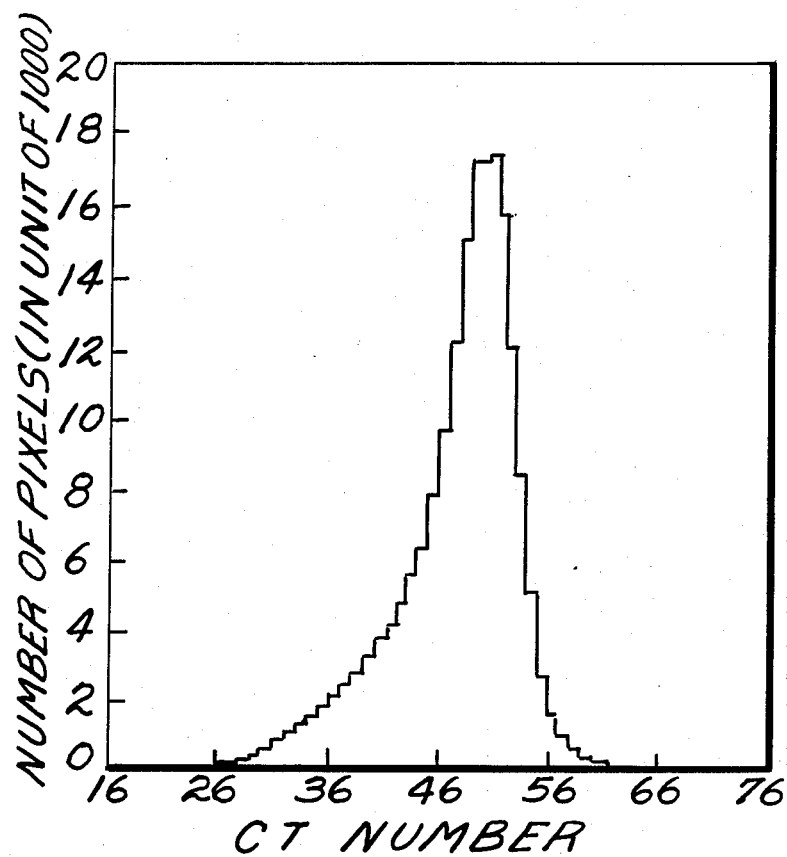
FIG. 4 is a representative histogram with a single peak for a patient with a relatively small tumor (581 cm$^2$).
Figure 5:
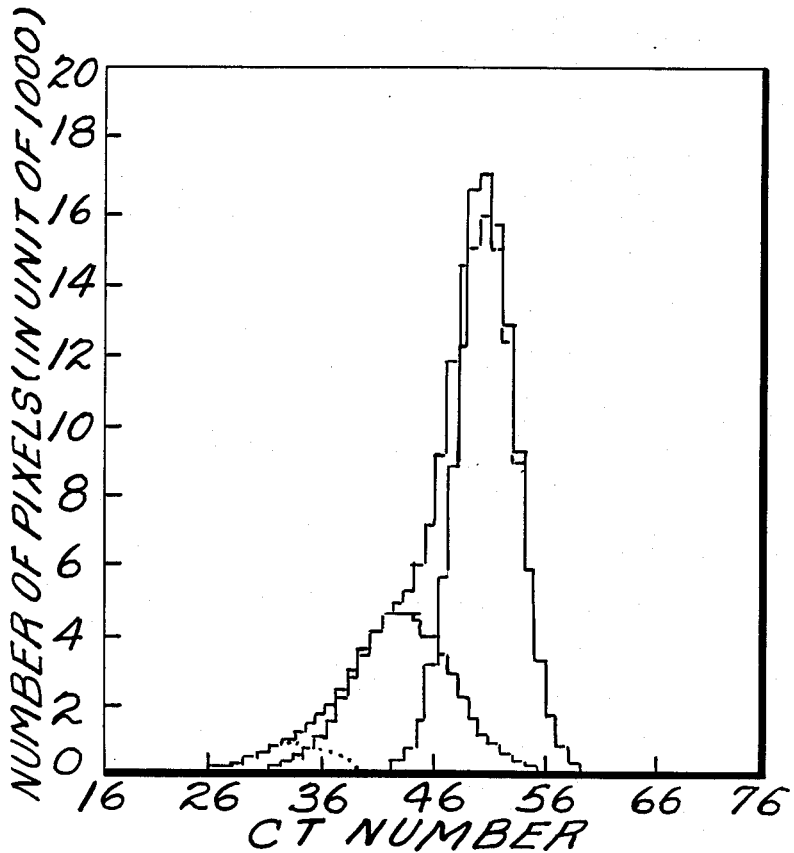
FIG. 5 is a global histogram (outside curve) of the CT number distribution for normal liver and tumor for the same patient as in FIG. 4.

A representative CT number distribution with a single peak for a patient with a small tumor is shown in FIG. 4. FIG. 5 shows the three gaussian functions and the histogram fit resulting from the addition of these functions. The three gaussian functions were summed to get the global histogram for this patient. The gaussian function with the largest amplitude and the highest mean CT number was representative of normal liver. The position of the arrow corresponded to one-fourth of the maximum of the dominant gaussian function (NL), and all pixels with CT numbers lower than this were empirically determined to be attributable to tumor For single-peak histograms and small tumors, the gaussian with the largest amplitude and highest mean CT number was very reproducible and represented normal liver. This gaussian had a standard deviation ranging from 2-6 Hounsfield Units (HU, 1000 scale). The gaussian with the second-largest amplitude and lower mean CT number had a standard deviation ranging from 3-10 HU. The lowest-amplitude gaussian had a more variable standard deviation and included pixels with low CT numbers and sometimes also those corresponding to tumor and normal liver.

Although in principle tumor volumes could be computed by summing pixels under the gaussian function with the second largest amplitude and lower mean CT number, in practice this was not feasible for the following reasons. The fitting parameters for the two lower-amplitude Gaussians could be varied considerably without significant changes in the goodness of the fit. The fit for these two functions was, therefore, not nearly as reproducible as for the dominant gaussian (NL) in FIG. 5. Secondly, highlighting of pixels in CT slices demonstrated that the gaussian with the second-largest amplitude included a large number of normal liver pixels as evidenced by the overlap of the fitting functions in FIG. 5.

An empirical method was, therefore, developed to compute tumor volumes based on the gaussian fitting function with the largest amplitude. This method was based on a quantitative comparison of tumor volume computations from global histograms and manually contoured CT slices. Volume determinations from manually contoured CT slices were carried out. Additionally, pixels corresponding to tumor were highlighted on CRT displays of CT slices and reviewed by experienced observers. For relatively small tumors, reproducible and satisfactory results were obtained by determining the CT number corresponding to one-fourth of the amplitude to the left of the mean of the gaussian function for normal liver of the (gaussian with the largest with the largest amplitude and the highest mean CT number), as indicated by the arrow in FIG. 5. All pixels to the left of the arrow, in the direction of lower CT numbers, were counted as tumor.

This procedure was justified because pixels with CT numbers above the threshold determined by left hand one-fourth of the amplitude of the dominant (NL) Gaussian had a high probability of representing normal liver tissue. For this threshold, Gaussian error analysis indicated that 95.2% of the normal liver Gaussian was above the threshold and occupied 1,395.63 area units. Using the tumor Gaussian in FIG. 5, 25.4% was above threshold and occupied 174.75 area units. Therefore, the probability of a normal liver pixel being above the threshold was 0.889 whereas the probability of a tumor pixel being above the threshold was 0.111.

Figure 6:
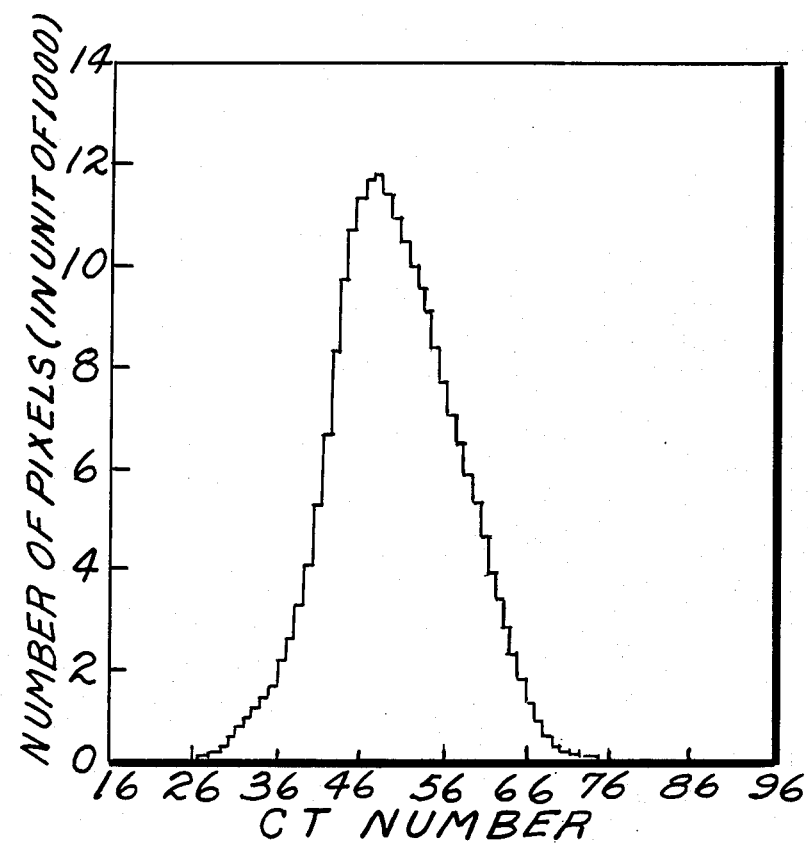
FIG. 6 is a representative histogram with single peak for a patient with a relatively large tumor (1687 cm$^3$).
Figure 7:
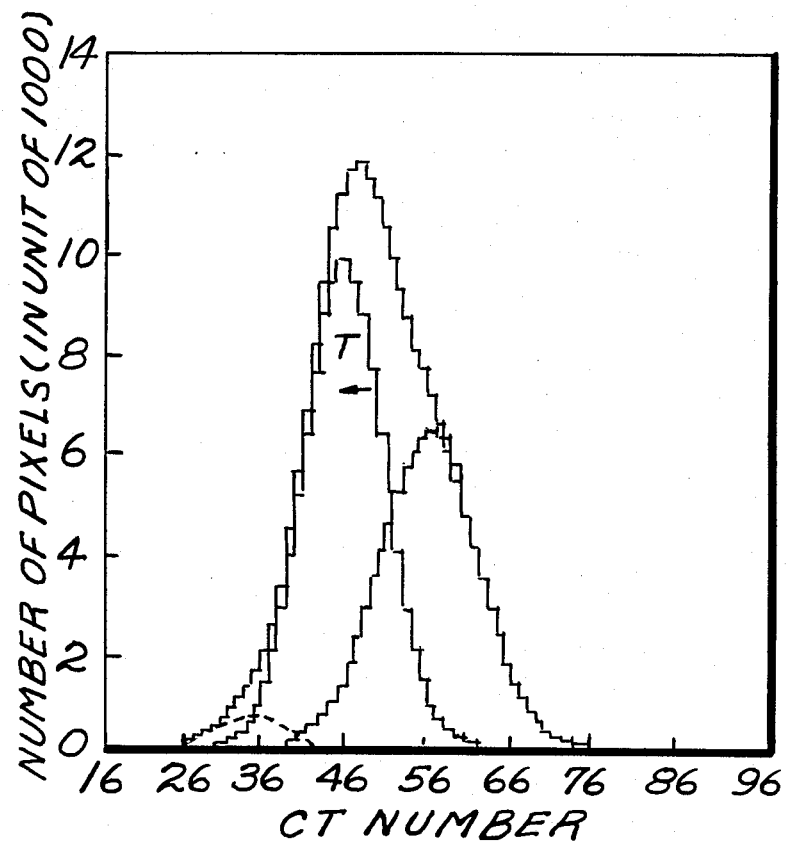
FIG. 7 is a global histogram (outside curve) for the same patient as in FIG. 6.

A global histogram for a patient with a large tumor is shown in FIG. 6. The three gaussians and the resulting histogram fit are displayed separately in FIG. 7. The gaussian with the largest amplitude and lower mean CT number was representative of the tumor, and the gaussian with the second largest amplitude and the highest mean CT number of normal liver. As before, the gaussian with the lowest amplitude and the lowest mean CT number extended from low CT numbers into the range corresponding to tumor and normal liver. For these large tumors, good results were obtained by determining the CT number corresponding to three-fourths of the amplitude to the right of the mean of the gaussian function for tumor, as indicated by the arrow in FIG. 7.

Tumor volumes were computed by summing over all pixels to the left of the arrow and multiplying by slice thickness.

The probability that a pixel below the threshold determined by three-fourths of the amplitude of the tumor Gaussian represented tumor tissue was estimated in the same manner as above. Namely, 77.6% of the tumor Gaussian was below the threshold and occupied 1,371.19 area units; 14.2% of the normal liver Gaussian in FIG. 7 was below the threshold and occupied 194.11 area units. In addition to that, the third Gaussian contributed 108 area units. Therefore, the probability of a tumor pixel, a normal liver pixel, or a non-tumorous low-density pixel being below the threshold was 0.820, 0.116, and 0.064, respectively.

Using a smaller fraction of the amplitude of the tumor Gaussian would have increased the probability of a tumor pixel below the threshold. However, this was equivalent to raising the CT number threshold for tumor pixels and had the undesirable effect of including normal liver in tumor volumes. This was ascertained by highlighting pixels in CT slices over a range of CT numbers of the tumor Gaussian.

Results of Study

Tumor and liver volumes of 51 patients with hepatoma and 5 patients with cholangiocarcinoma were computed from CT scans. The procedures for volume determinations were the same for these two groups of patients. For the first consecutive 10 patients, volumes computed from manually contoured CT slices were compared with volumes obtained by the global histogram method.

Figure 8A:
FIG. 8(a) is a representative CT slice of a patient with a solid hepatoma. The tumor (dark area) was highlighted according to the global histogram method.
Figure 8B:
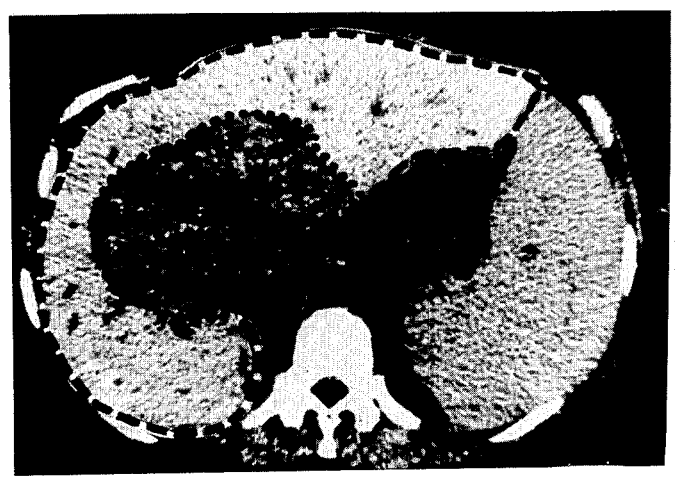
FIG. 8(b) is the same CT slice as in FIG. 8(a), but manually contoured by an experienced observer.

FIG. 8(a) shows a CT slice of a hepatoma patient with a solid tumor and tumor pixels highlighted according to the global histogram for this patient. For comparison, the same slice is shown in FIG. 8(b) with the liver and tumor-bearing region defined manually by an experienced observer directly on the CT film. Results obtained by these two methods are shown in FIGS. 9 and 10 for liver and tumor volumes, respectively.

Figure 9:
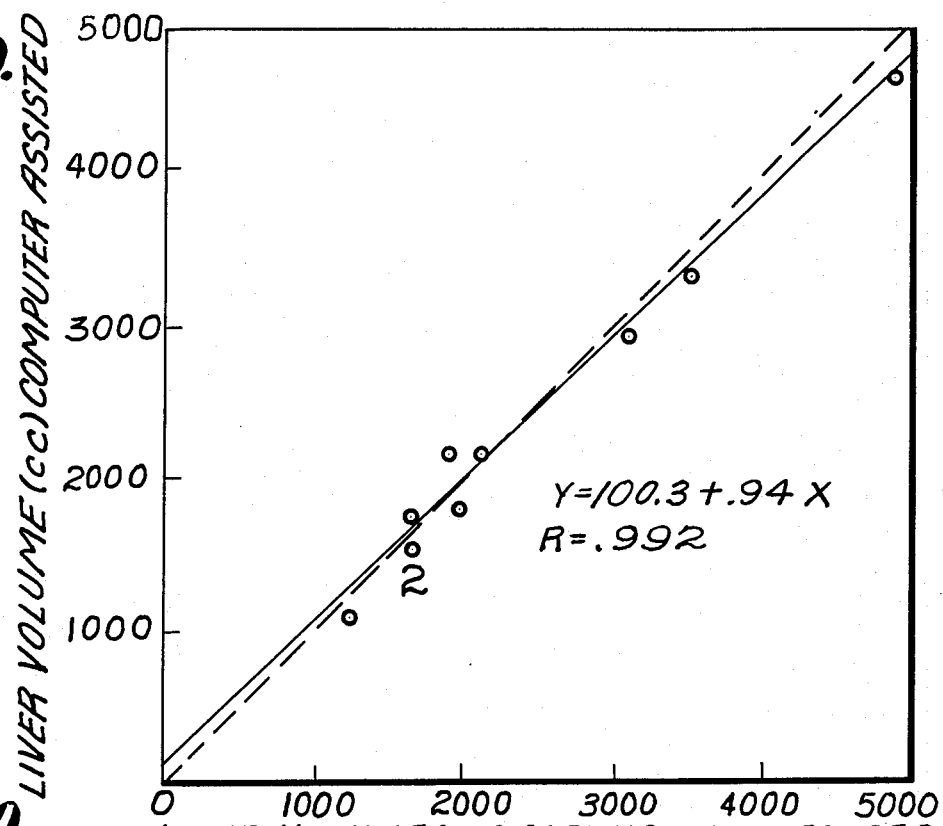
FIG. 9 is a comparison of liver volumes obtained by the global histogram method (computer assisted) and from manually contoured CT slices for a sample of 10 patients.

FIG. 9 is a comparison of liver volumes obtained by the global histogram method (computer assisted) and from manually contoured CT slices for a sample of 10 patients. Two of the volumes were nearly identical, as indicated by the number 2. The solid line was generated from a least-squares fit with a correlation coefficient of 0.992. The dashed line is the line of identity.

Figure 10:
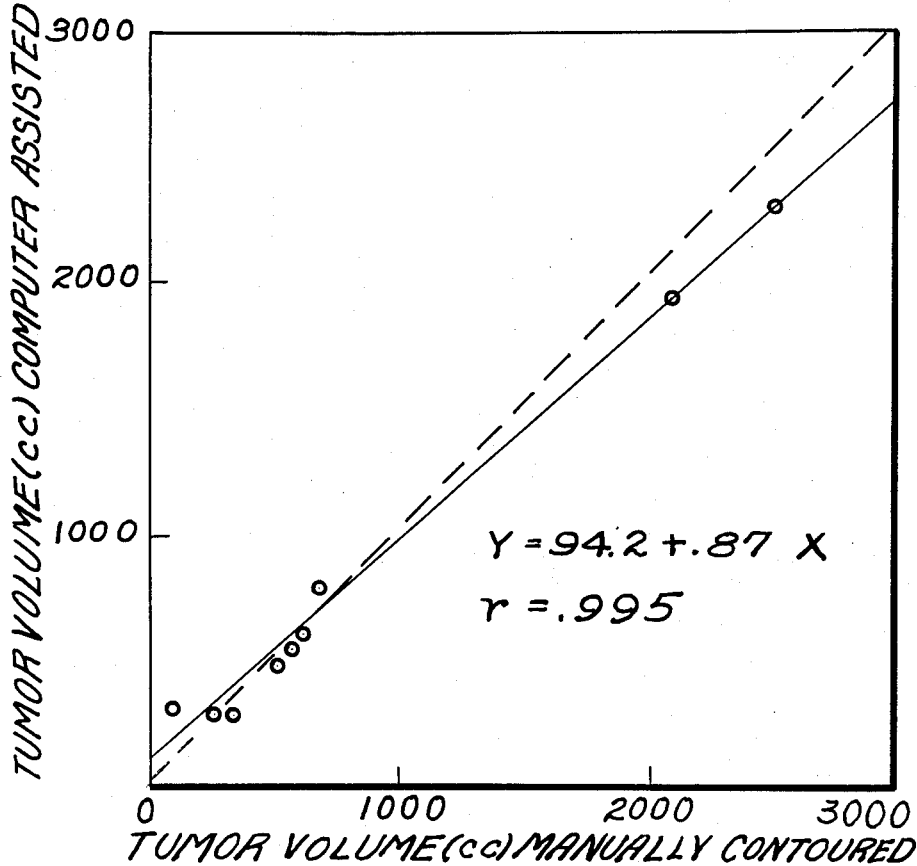
FIG. 10 is a comparison of tumor volumes computed by the global histogram method and from manually contoured CT slices for the same patients as in FIG. 9.

FIG. 10 is a comparison of tumor volumes computed by the global histogram method and from manually contoured CT slices for the same patients as in FIG. 9. The correlation coefficient was 0.995 (solid line). The dashed line is the line of identity. For both liver and tumor volumes, results were clustered about the line of identity with correlation coefficients of 0.992 (liver) and 0.995 (tumor).

Figure 11A:
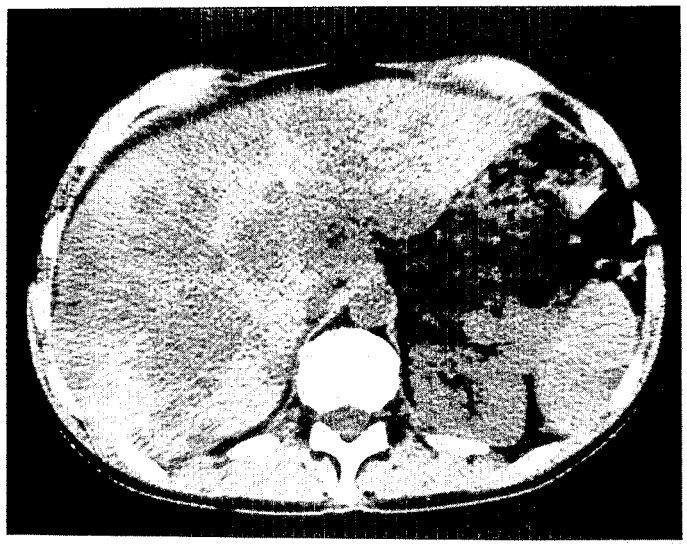
FIG. 11(a) is a CT slice of a patient with diffuse hepatoma.
Figure 11B:
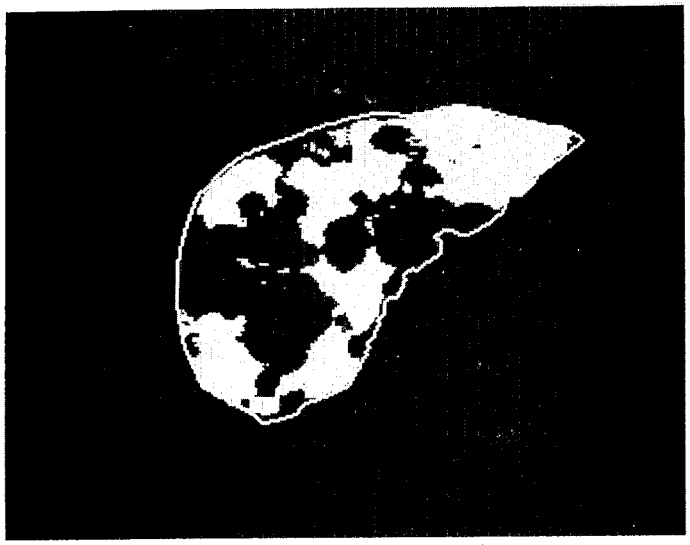
FIG. 11(b) is the same slice as in FIG. 11(a) but with tumor bearing regions highlighted according to the global histogram method.

For the remaining 46 patients, normal and tumor pixels in CT slices were highlighted and displayed on a color monitor. A representative CT slice of patient with diffuse hepatoma that would have been difficult to contour manually is shown in FIG. 11(a) The same slice highlighted according to the global histogram method is shown in FIG. 11(b). Normal liver and tumor ROI's in CT slices for this and all other patients were reviewed by experienced observers and determined to be satisfactory.

Global histogram structures of the CT numbers for 51 patients with hepatoma and 5 patients with cholangiocarcinoma are summarized in Table 1.

TABLE 1

| Global histogram structures of CT numbers for patients with hepatoma and cholangiocarcinoma | | |
|---|---|---|
| Histogram | Number of Patients | |
| Structure | Hepatoma | Cholangiocarcinoma |
| Single peak | 34 | 3 |
| Double peak | 15 | 2 |
| Triple peak | 2 | 0 |

Thirty-seven (66%) of these patients had histograms that were characterized by a single peak (FIGS. 4 and 6), 17 (30%) had double-peak, and 2 (4%) had triple-peak histograms (FIGS. 2 and 3).

Figure 12:
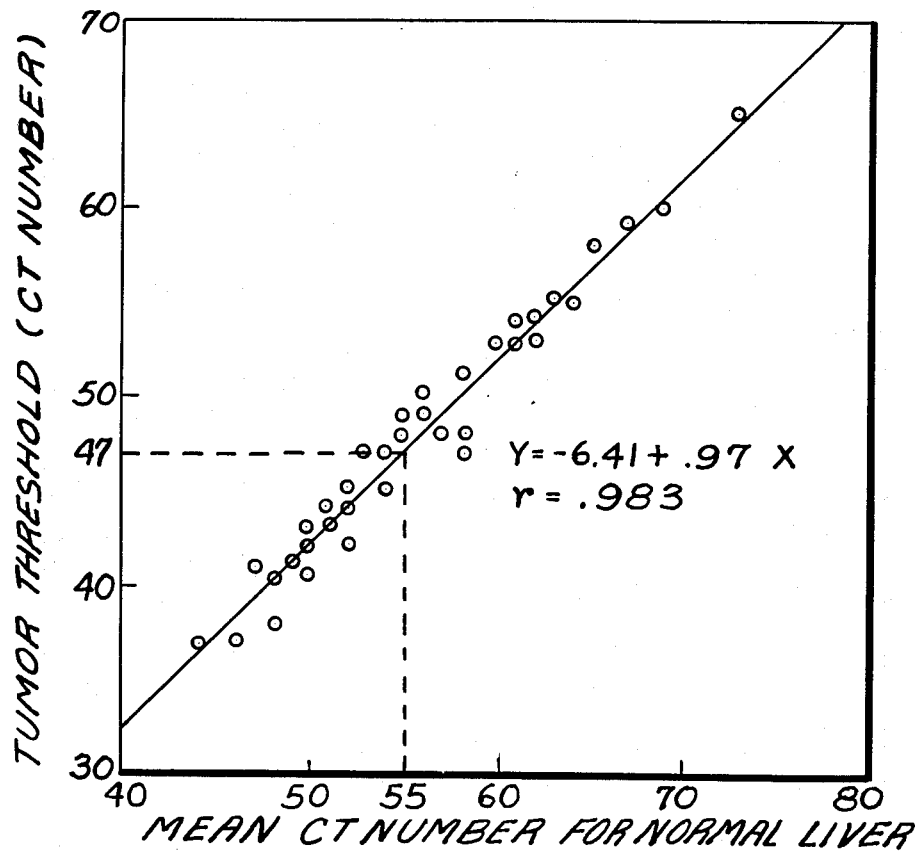
FIG. 12 shows the relationship between mean CT numbers of normal liver tissue and the threshold values of CT numbers used in tumor volume computations for global histograms characterized by a single peak.

FIG. 12 shows the relationship between mean CT numbers of normal liver tissue and the threshold values of CT numbers used in tumor volume computations for global histograms characterized by a single peak. An example is indicated by the dashed lines. The mean CT number for normal liver is 55 HU and the corresponding threshold CT number for tumor computations is 47 HU. Also shown is the least-squares fit line.

FIG. 12 demonstrates the relationship between mean CT numbers of normal liver tissue and the threshold values of CT numbers used in tumor volume computations, based on global histograms characterized by a single based on global peak. For this group of patients, mean CT numbers for normal liver ranged from 44-73 HU, whereas threshold CT numbers for tumors ranged from 37-65 HU. An illustration of this relationship is indicated by the dashed lines in FIG. 12. In this example, the mean CT number for normal liver is 55 HU, and the corresponding threshold CT number for tumor volume computations is 47 HU. All pixels with CT numbers less than or equal to 47 HU would be counted as tumor.

Figure 13:
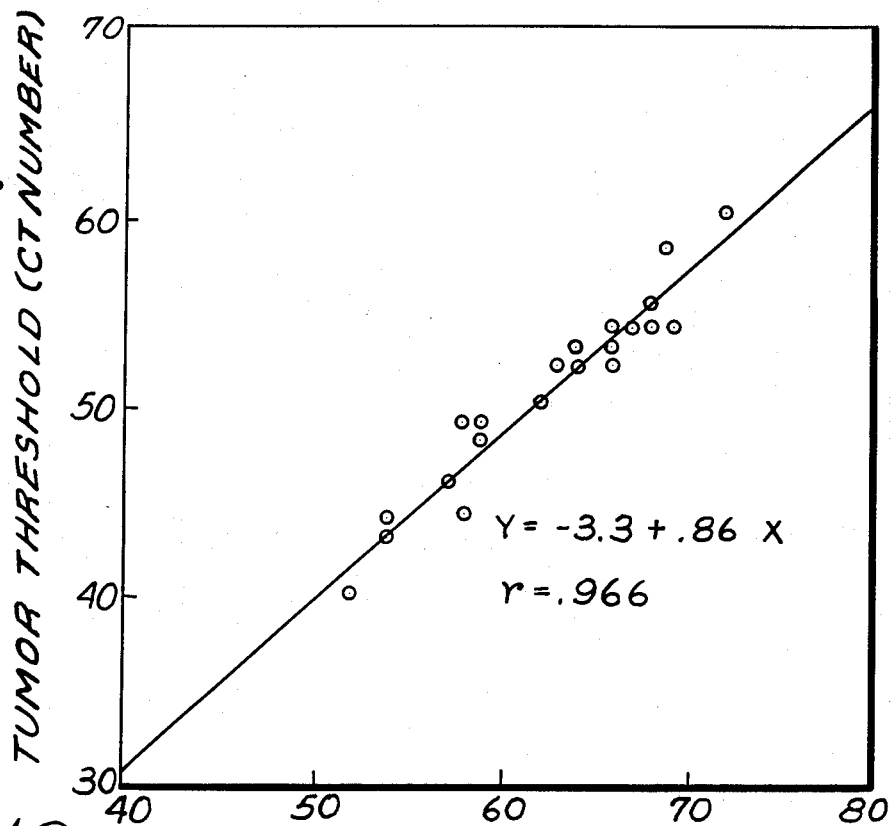
FIG. 13 shows the relationship between mean CT numbers for normal liver and threshold CT numbers used in tumor computations for histograms which were characterized by two and three distinct peaks.

FIG. 13 shows the relationship between mean CT numbers for normal liver and threshold CT numbers used in tumor computations for histograms which were characterized by two and three distinct peaks. Also shown is the least-squares fit line.

For these CT number distributions, mean CT numbers for normal liver ranged from 52-72 HU, and tumor threshold value from 40-60 HU. These data showed that for all types of global histograms encountered, there was a nearly linear relationship between mean CT numbers for normal liver and threshold CT numbers for tumor volume computations.

The number of CT examinations in FIGS. 12 and 13 included patients who were scanned prior to and following therapy. There were, however, no systematic changes in either the mean CT number for normal liver or the threshold CT number for tumor volume computations following therapy.

An example of the clinical application of liver and hepatoma volume calculations is provided by the data in Table 2.

TABLE 2

| CT liver and hepatoma volume computations prior to and following I-131 labeled antiferritin IgG treatments | | | | | |
|---|---|---|---|---|---|
| CT scan No. | Treatment No. | Liver Volume (cm$^2$) | Percent* Change | Hepatoma Volume (cm$^2$) | Percent* Change |
| 1 | | 3288 | — | 2480 | |
| 2 | 1 | 1756 | −46.6 | 891 | −64.1 |

TABLE 2-continued

CT liver and hepatoma volume computations prior to and following I-131 labeled antiferritin IgG treatments

| CT scan No. | Treatment No. | Liver Volume (cm³) | Percent* Change | Hepatoma Volume (cm²) | Percent* Change |
|---|---|---|---|---|---|
| 3 | 2 | 1344 | −23.5 | 501 | −43.8 |
| 4 | 3 | 1123 | −16.4 | 298 | −40.1 |

*Percent change in volume as compared to previous CT scan.

Liver and tumor volume computations were made prior to and following three administrations of I-131 labeled antiferritin IgG. After the third treatment, the tumor volume had been reduced from 2480 cm³ to 298 cm³, and the patient underwent surgery for removal of the residual tumor.

To assess tumor response to a given therapy, accurate and timely tumor volume computations are required. Such computations are essential in planning treatment strategies and making appropriate changes in therapy, if required. Computer assisted volume computations have proven to be clinically important for these reasons and because of their reproducibility. Repeat volume computations by different observers were consistent to within 2-4%. Additionally, the semi-automatic ROI software was faster than manual outlining using a track ball, light pen, cursor, etc., to define boundaries. This is of considerable practical importance when analyzing large numbers of CT slices in ongoing clinical trials.

The technique according to the present invention is independent of the mean CT number for normal liver in individual slices, it is readily applicable to tumors which have invaded normal liver diffusely and for which single-slice statistics are less reliable. The global histogram approach also makes it possible to define a relationship for the mean CT number associated with normal liver and threshold CT numbers for volume determinations of hepatic tumors.

The use of computer-assisted volume determination has its limitations. With a slice thickness of 8 mm, partial volume effects introduce a small error in volume computations. We estimated this effect by summing over the first and last slices and dividing by two. The variation due this procedure ranged from 0.36-1.9% of total liver volume. As detailed in Moss AA, Cann CE, Friedman MA, Marcus FS, Resser KJ, Berninger W. Volumetric CT analysis of hepatic tumors. J Comput Assist Tomogr 1981;5:714-8 and Ettinger DS, Leichner PK, Siegelman SS, et al. Computed tomography assisted volumetric analysis of primary liver tumor as a measure of response to therapy. Am J Clin Oncol 1985;8:413-8, non-tumorous structures of low density such as bile ducts, portal and hepatic vessels, and fatty tissues are included in tumor volumes. An estimate of this error was obtained by summing over the third gaussian distribution separately. It was determined that for most patients, this gaussian contributed 0.50-5.89% to the liver volumes. In 2.5% of the patients, the CT number distributions were irregular and could not be fit to three gaussians. In spite of these limitations, a comparison of computed liver and tumor volumes and autopsy data of 4 patients with primary hepatic liver cancers showed a maximum difference of +/−6.4% {See Ettinger DS, Leichner PK, Siegelman SS, et al. Computed tomography assisted volumetric analysis of primary liver tumor as a measure of response to therapy. Am J Clin Oncol 1985;8:413-8}. This was consistent with the estimated errors in the present work.

Other embodiments of the invention should occur to those of ordinary skill in the art having the benefit of the teachings presented herein. Therefore such alternative embodiments are intended to be within the scope of the claims herein.

I claim:

TUMOR VOLUME DETERMINATION

APPENDIX I

Software Listing

The following is a listing of the software for carrying out the claimed invention.

```
C       THIS PROGRAM WAS WRITTEN TO DRAW THE LIVER CONTOUR ON
C       EACH CT SLICE AND CALCULATE THE VOLUME OF IT
C       @ COPYRIGHT 1985,NAI-CHUEN YANG,PH. D.  AND PETER K LEICHNER,PH D
        COMMON/XYZ/IA2, IBUFF, JBUFF
        COMMON/ABC/IX1, IY1, ICOUNT, ISAVE(2000)
        COMMON/MAXIN/IMIN, IMAX, JMIN, JMAX
        COMMON/DEF/LOWER, UPPER
        COMMON/GHI/ICAL
        COMMON/JKL/IX, IY
        COMMON/HIST/NHIS
        COMMON/Z/IBNK
        COMMON//HB(10000)
C       COMMON BLOCK FOR THE HISTOGRAM
        CHARACTER*1 IBLANK, ILAST, ICUR, ICAL, IBNK
        CHARACTER*1 AB(1600)
        CHARACTER*2 CHAR1
        CHARACTER*3 CHAR2
        CHARACTER*4 CHAR3
        CHARACTER*30 NAME
        BYTE LOWER, UPPER
        INTEGER*2 IX(10), IY(10)
        BYTE IA2(256,256), IBUFF(256,256), JBUFF(256,256)
C       INITIALIZING THE DMA
        CALL RTINIT('DMA',3)
C       INITIALIZING THE RANGE OF THE CT NUMBERS IN HISTOGRAMS WITH 100 BINS
        CALL HBOOKI(1,'CT NUMBERS$',100,1.,101.,0.)
        CALL HBOOKI(2,'CT NUMBERS$',100,1.,101.,0.)
        NHIS=2
        NBOUN=0
3       CONTINUE
        WRITE(6,2)
2       FORMAT(X,'ENTER THE DATASET NAME')
```

```
C       READ IN THE FILTERED CT DATA SLICE BY SLICE
        READ(5,1)NAME
1       FORMAT(A30)
        IF(NAME.EQ.'DONE')GO TO 1000
        OPEN(UNIT=80,FILE=NAME,STATUS='OLD',READONLY,SHARED,
       1    FORM='UNFORMATTED')
        READ(80)A8,IA2
C       A8 IS THE ID BLOCK AND IA2 IS THE 256X256 IMAGE MATRIX
        WRITE(6,31)(A8(K),K=980,1050)
31      FORMAT(1X,80A1)
        CALL ENTGRA
        CALL MOVABS(-128,127)
        CALL PIXELB(256,256,IA2)
        CALL QUIT
C       THE CONTOUR DUE TO THE LAST SLICE CAN BE USED AS A GUIDE TO THE RECENT SLICE
12      TYPE *,'DO YOU WANT TO USE LAST BOUNDARY ?,Y/N'
        READ(5,5)ILAST
        IF(ILAST.EQ.'N')GO TO 11
        CALL LAST
        CALL BLTEST(IBNK)
C       BLANK THE OUTSIDE AREA OF THE OLD CONTOUR
        TYPE *,'DO YOU WANT TO BLANK THE OUTSIDE AREA ?,Y/N'
        READ(5,5)IBLANK
5       FORMAT(A2)
        IF(IBLANK.EQ.'Y')CALL BLANK
C       USE THE CURSER TO FIND THE START POINT AND BLANKING UNNECESSARY AREAS
11      TYPE *,'DO YOU WANT TO USE CURSER?, Y/N'
        READ(5,5)ICUR
        IF(ICUR.EQ.'Y')CALL CURSER
33      CONTINUE
        TYPE *,'ENTER LOWER AND UPPER LIMITS OF CT NUMBERS'
        ACCEPT *,LOWER,UPPER
C       IF(LOWER.EQ.999)GO TO 3
        TYPE *,'ENTER THE STARTING POINT'
        CALL CURSER
        IX1=IX(1)
        IY1=IY(1)
        CALL TRACE
        TYPE *,'DO YOU WANT TO CALCULATE THE VOLUME?,Y/N'
        READ(5,5)ICAL
        IF(ICAL.EQ.'Y')GO TO 44
C       IF THE CONTOUR IS UNSATISFIED,GO BACK AND REDRAW IT
        GO TO 11
44      CONTINUE
        NBOUN=NBOUN+1
        IF(NBOUN.EQ.1)THEN
        CHAR1=NAME(9:10)
        CHAR2='B'//CHAR1
        OPEN(UNIT=1,FILE=CHAR2,STATUS='NEW',FORM='UNFORMATTED')
C       SAVE THE BOUNDARY POINTS OF THE FINAL CONTOUR WITH DATA SET NAME B*.DAT, *=02,03
        WRITE(1)ICOUNT,(ISAVE(K),K=1,ICOUNT)
        END IF
        IF(NBOUN.EQ.2)THEN
        CHAR3='NB'//CHAR1
        OPEN(UNIT=2,FILE=CHAR3,STATUS='NEW',FORM='UNFORMATTED')
        WRITE(2)ICOUNT,(ISAVE(K),K=1,ICOUNT)
        END IF
        CALL BLTEST(IBNK)
C       CALCULATE THE VOLUME IN TERMS OF THE TOTAL PIXEL NUMBER ON THAT SLICE
        NHIS=NHIS+1
        CALL VOLUME(IVOL)
        TYPE *,'NUMBER OF PIXELS OF THE LIVER IN THIS SLICE=',IVOL
        IF(NHIS.EQ.3)THEN
        CHAR2='H'//CHAR1
        OPEN(UNIT=3,FILE=CHAR2,STATUS='NEW',FORM='UNFORMATTED')
C       HISTOGRAM 1 WAS WRITTEN ON UNIT 3 WITH NAME H*.DAT, *=02,03
        CALL HSTORE(1,3)
        END IF
        IF(NHIS.EQ.4)THEN
        CHAR3='NH'//CHAR1
        OPEN(UNIT=4,FILE=CHAR3,STATUS='NEW',FORM='UNFORMATTED')
C       HISTOGRAM 2 WAS WRITTEN ON UNIT 4 WITH NAME NH*.DAT, *=02,03
        CALL HSTORE(2,4)
        END IF
        GO TO 11
1000    STOP
        END
C       THIS SUBROUTINE WAS WRITTEN TO MOVE THE CURSER TO ANY POINT (IXX,IYY) AND FIND OUT THE CT NUMBER ON THAT POINT
C       ALSO IT CAN BE USED TO BLANK CERTAIN AREA BY SPECIFYING TWO POINTS
        SUBROUTINE CURSER
        COMMON/JKL/IX,IY
        INTEGER*2 IX(10),IY(10)
        INTEGER*2 IXX,IYY,JRED,JGRN,JBLU
        DO K=1,10
        IX(K)=0
        IY(K)=0
        END DO
C       SET UP THE CROSS-HAIR CURSER AND DEFINE THE MACRO TO PUSH THE BUTTON ON THE DIGITIZER
        CALL ENTGRA
        CALL XHAIR(0,1)
        CALL MACDEF(10)
        CALL CMOVE(5,2)
        CALL MACEND
        CALL BUTTBL(0,10)
        CALL QUIT
        IBUTT=0
1       NCOUNT=0
10      CONTINUE
        NCOUNT=NCOUNT+1
C       READ THE CURSER POSITION (IXX,IYY) AND THE PIXEL VALUE, IBUTT=BUTTON NUMBER
        CALL ENTGRA
        CALL READBU(1,1,IBUTT,IXX,IYY)
        CALL MOVABS(IXX,IYY)
        CALL READP(JRED,JGRN,JBLU)
        CALL QUIT
C       JRED=PIXEL VALUE, JGRN=JBLU=0
        WRITE(6,100)IXX,IYY,JRED
        IF(NCOUNT.GT.10)GO TO 1
        IX(NCOUNT)=IXX
        IY(NCOUNT)=IYY
100     FORMAT(1X,5I10)
C       PUSH BUTTON 3 TO GET OUT OF THE CURSOR MODE
        IF(IBUTT.EQ.3)GO TO 999
        IF(IBUTT.GE.7)NCOUNT=0
        IF(IBUTT.EQ.7)CALL BLKG(IX(1),IX(2))
        IF(IBUTT.EQ.9)CALL BLKR(IY(1),IY(2))
        IF(IBUTT.EQ.8)CALL BLKL(IY(1),IY(2))
        IF(IBUTT.EQ.10)CALL BLKU(IX(1),IX(2))
```

```
      IF(IBUTT.EQ.11)CALL BLKD(IX(1),IX(2))
      IF(IBUTT.EQ.13)CALL BLINER(IX(1),IY(1),IX(2),IY(2))
      IF(IBUTT.EQ.12)CALL BLINEL(IX(1),IY(1),IX(2),IY(2))
      IF(IBUTT.EQ.14)CALL BLINEU(IX(1),IY(1),IX(2),IY(2))
      IF(IBUTT.EQ.15)CALL BLINED(IX(1),IY(1),IX(2),IY(2))
      IF(IBUTT.GE.7)TYPE *,'PLEASE GO ON'
      GO TO 10
999   CONTINUE
      RETURN
      END
C     THIS SUBROUTINE WAS WRITTEN TO OVERLAY AN EXISTED CONTOUR ON THE RECENT IMAGE
      SUBROUTINE LAST
      DIMENSION JSAVE(2000)
      COMMON/GHI/ICAL
      COMMON/XYZ/IA2,IBUFF,JBUFF
      COMMON/ABC/IX1,IY1,ICOUNT,ISAVE(2000)
      BYTE IA2(256,256),IBUFF(256,256),JBUFF(256,256)
      CHARACTER*30 NAME
      CHARACTER*1 ICAL
      ICAL='N'
      ICOUNT=0
      TYPE *,'ENTER THE LAST DATASET NAME'
      READ(5,1)NAME
1     FORMAT(A30)
      OPEN(UNIT=9,FILE=NAME,STATUS='OLD',READONLY,SHARED,
     1    FORM='UNFORMATTED')
      READ(9)JCOUNT,(JSAVE(KK),KK=1,JCOUNT)
C     THE SAVE DATA JSAVE(K) WAS ENCODED AS JSAVE=I*1000+J,
C     WHERE I,J ARE MATRIX INDEX AND ARE RELATED TO IX,IY ON THE SCREEN BY I=IX+129,J=128-IY
      DO 5000 KK=1,JCOUNT
      II=JSAVE(KK)/1000
      JJ=MOD(JSAVE(KK),1000)
C     SET UP A FLAG TO BE A BOUNDARY POINT
      JBUFF(II,JJ)=2
      IF(KK.NE.JCOUNT)THEN
      MM=JSAVE(KK+1)/1000
      NN=MOD(JSAVE(KK+1),1000)
      END IF
      IF(KK.EQ.JCOUNT)THEN
      MM=JSAVE(1)/1000
      NN=MOD(JSAVE(1),1000)
      END IF
      CALL DRAW(II,JJ,MM,NN)
5000  CONTINUE
      RETURN
      END
C     THIS SUBROUTINE WAS WRITTEN TO DETERMINE THE DIRECTION
C     OF THE CONTOUR
      SUBROUTINE BLTEST(KBLANK)
      COMMON/ABC/IX1,IY1,ICOUNT,ISAVE(2000)
      INTEGER*2 II(30),JJ(30)
      CHARACTER*1 KBLANK
      DO L=1,30
      II(L)=ISAVE(L)/1000
      JJ(L)=MOD(ISAVE(L),1000)
      END DO
      IFIRST=1
10    IUP=0
      IDOWN=0
      DO K=IFIRST+1,ICOUNT
      I=ISAVE(K)/1000
      J=MOD(ISAVE(K),1000)
      IF(I.EQ.II(IFIRST).AND.J.LT.JJ(IFIRST))IUP=IUP+1
      IF(I.EQ.II(IFIRST).AND.J.GT.JJ(IFIRST))IDOWN=IDOWN+1
      END DO
      MU=MOD(IUP,2)
      MD=MOD(IDOWN,2)
      IF(MD.EQ.MU)THEN
      IFIRST=IFIRST+1
      GO TO 10
      END IF
      IF(MU.EQ.1.AND.MD.EQ.0.AND.II(IFIRST).GT.II(IFIRST+1))KBLANK='C'
      IF(MU.EQ.0.AND.MD.EQ.1.AND.II(IFIRST).LT.II(IFIRST+1))KBLANK='C'
      IF(MU.EQ.1.AND.MD.EQ.0.AND.II(IFIRST).LT.II(IFIRST+1))KBLANK='A'
      IF(MU.EQ.0.AND.MD.EQ.1.AND.II(IFIRST).GT.II(IFIRST+1))KBLANK='A'
      IF(KBLANK.EQ.'C')TYPE *,'THIS IS A CLOCKWISE CONTOUR'
      IF(KBLANK.EQ.'A')TYPE *,'THIS IS AN ANTI-CLOCKWISE CONTOUR'
      RETURN
      END
C     THIS SUBROUTINE WAS WRITTEN TO DRAW A LINE BETWEEN TWO PIXELS (II,JJ) AND (MM,NN)
      SUBROUTINE DRAW(II,JJ,MM,NN)
      COMMON/ABC/IX1,IY1,ICOUNT,ISAVE(2000)
      COMMON/MAXIN/IMIN,IMAX,JMIN,JMAX
      COMMON/GHI/ICAL
      CHARACTER*1 ICAL
C     ICOUNT WAS SET TO ZERO AT THE BEGINNING OF THE SUBROUTINE LAST AND THE SUBROUTINE TRACE
      ICOUNT=ICOUNT+1
      ISAVE(ICOUNT)=II*1000+JJ
      IF(ICOUNT.EQ.1)THEN
      IMIN=II
      IMAX=II
      JMIN=JJ
      JMAX=JJ
      END IF
C     CALCULATE THE MINIMA AND MAXIMA INDEX OF THE BOUNDARY POINTS
      IF(II.LT.IMIN)IMIN=II
      IF(II.GT.IMAX)IMAX=II
      IF(JJ.LT.JMIN)JMIN=JJ
      IF(JJ.GT.JMAX)JMAX=JJ
      IXO=II-129
      IYO=128-JJ
      IX=MM-129
      IY=128-NN
      CALL ENTGRA
      CALL MOVABS(IXO,IYO)
      IF(ICOUNT.EQ.1)THEN
      IFEQ=IFEQ+1
      IF(IFEQ.GT.7)IFEQ=IFEQ-7
      IF(IFEQ.EQ.1)CALL VALUE(255,0,0)
      IF(IFEQ.EQ.2)CALL VALUE(0,255,0)
      IF(IFEQ.EQ.3)CALL VALUE(0,0,255)
      IF(IFEQ.EQ.4)CALL VALUE(255,255,0)
      IF(IFEQ.EQ.5)CALL VALUE(255,0,255)
      IF(IFEQ.EQ.6)CALL VALUE(0,255,255)
      IF(IFEQ.EQ.7)CALL VALUE(255,255,255)
      END IF
      CALL DRWABS(IX,IY)
      CALL QUIT
```

```
        RETURN
        END
C       THIS SUBROUTINE WAS WRITTEN TO BLANK THE OUTSIDE AREA OF THE EXISTED CONTOUR BY USING PARITY METHOD
        SUBROUTINE BLANK
        COMMON/Z/IBNK
        COMMON/ABC/IX1,IY1,ICOUNT,ISAVE(2000)
        COMMON/XYZ/IA2,IBUFF,JBUFF
        CHARACTER*1 IBNK
        BYTE IA2(256,256),IBUFF(256,256),JBUFF(256,256)
        DO K=1,ICOUNT
        I=ISAVE(K)/1000
        J=MOD(ISAVE(K),1000)
        IF(K.EQ.1)THEN
        IIMIN=I
        IIMAX=I
        JJMIN=J
        JJMAX=J
        END IF
        IF(I.LT.IIMIN)IIMIN=I
        IF(I.GT.IIMAX)IIMAX=I
        IF(J.LT.JJMIN)JJMIN=J
        IF(J.GT.JJMAX)JJMAX=J
C       TEST THE PARITY OF THE Kth POINT PARITY=1 MEANS THAT IT IS THE EXTREME POINT OF THE GAP WHEN CROSSING
C       THE CONTOUR TO CALCULATE THE VOLUME, WHILE FOR PARITY=0, IT IS NOT AN EXTREME POINT
        CALL TPARITY(K,IP)
C       SAVE THE PARITY OF EACH POINT IN THE ARRAY IBUFF. SOME POINT MAY BE CLOSED TWICE, SO IT NEEDED TO BE SUMMED
        IBUFF(I,J)=IBUFF(I,J)+IP
        END DO
        DO JJ=JJMIN-10,JJMAX+10
        IFLAG=0
        IPAR=0
        DO II=IIMIN-10,IIMAX+10
C       TEST THE TOTAL PARITY OF EACH POINT, IBUFF(II,JJ)=EVEN (IBUFF=0,2) MEANS THAT IT IS NOT AN EXTREME POINT OR
C       IT IS A DEGENERATE EXTREME POINT (IBUFF=2) AND IS NOT NECESSARY TO TAKE INTO ACCOUNT FOR GAP CROSSING
C       IBUFF(II,JJ)=ODD (IBUFF=1) MEANS THAT IT IS AN EXTREME POINT FOR GAP CROSSING AND SHOULD BE TAKEN INTO ACCOUNT
        IF(IBUFF(II,JJ).EQ.1)THEN
C       IFLAG IS THE FLAG TO COUNT HOW MANY EXTREME POINTS HAS BEEN ENCOUNTERED WHEN CROSSING THE ROW JJ FROM COLUMNS IMIN TO IMAX
        IFLAG=IFLAG+1
C       IPAR IS THE PARAMETER TO POINT OUT THAT IT HAS CROSSED EVEN OR ODD TIMES ON THE BOUNDARY
        IPAR=MOD(IFLAG,2)
        END IF
C       ZERO THE PIXELS OUTSIDE THE BOUNDARY
        IF(IPAR.EQ.0.AND.IBUFF(II,JJ).EQ.0)THEN
        IA2(II,JJ)=0
        END IF
        IF(IBUFF(II,JJ).GT.0)IBUFF(II,JJ)=0
        END DO
        END DO
        RETURN
        END
C       THIS SUBROUTINE WAS WRITTEN TO TEST THE PARITY OF THE BOUNDARY POINT NUM AND RETURN ITS PARITY
C       IT NEEDS THE POINT BEFORE AND THE POINT AFTER THE SPECIFIC POINT TO CHECK THE PARITY AND
C       DEPENDS ON THE DIRECTION (CLOCKWISE OR ANTI-CLOCKWISE) OF THE CONTOUR
        SUBROUTINE TPARITY(NUM,IPARITY)
        COMMON/ABC/IX1,IY1,ICOUNT,ISAVE(2000)
        COMMON/Z/IBNK
        CHARACTER*1 IBNK
        NUM1=NUM-1
        NUM2=NUM+1
        IF(NUM.EQ.1)NUM1=ICOUNT
        IF(NUM.EQ.ICOUNT)NUM2=1
C       (I,J) IS THE SPECIFIC POINT
        I=ISAVE(NUM)/1000
        J=MOD(ISAVE(NUM),1000)
C       (I1,J1) IS THE POINT BEFORE
        I1=ISAVE(NUM1)/1000
        J1=MOD(ISAVE(NUM1),1000)
C       (I2,J2) IS THE POINT AFTER
        I2=ISAVE(NUM2)/1000
        J2=MOD(ISAVE(NUM2),1000)
        IPARITY=1
        LI2=I2-I
        LI1=I-I1
        LJ2=J2-J
        LJ1=J-J1
C       THE SINGULAR BOUNDARY POINTS HAVE PARITY=10
        IF(J2.EQ.J1)IPARITY=10
C       DIFFERENT TYPES OF POINTS WHICH HAVE PARITY EQUAL TO ZERO FOR A CLOCKWISE CONTOUR
        IF(IBNK.EQ.'C')THEN
        IF(LJ1.EQ.0.AND.LJ2.EQ.-1.AND.LI1.EQ.1)IPARITY=0
        IF(LJ1.EQ.1.AND.LJ2.EQ.0.AND.LI2.EQ.1)IPARITY=0
        IF(LJ1.EQ.0.AND.LJ2.EQ.1.AND.LI1.EQ.-1)IPARITY=0
        IF(LJ1.EQ.-1.AND.LJ2.EQ.0.AND.LI2.EQ.-1)IPARITY=0
        END IF
C       DIFFERENT TYPES OF POINTS WHICH HAVE PARITY EQUAL TO ZERO FOR AN ANTI-CLOCKWISE CONTOUR
        IF(IBNK.EQ.'A')THEN
        IF(LJ1.EQ.1.AND.LJ2.EQ.0.AND.LI2.EQ.-1)IPARITY=0
        IF(LJ1.EQ.0.AND.LJ2.EQ.-1.AND.LI1.EQ.-1)IPARITY=0
        IF(LJ1.EQ.-1.AND.LJ2.EQ.0.AND.LI2.EQ.1)IPARITY=0
        IF(LJ1.EQ.0.AND.LJ2.EQ.1.AND.LI1.EQ.1)IPARITY=0
        END IF
        RETURN
        END
C       THIS SUBROUTINE WAS WRITTEN TO TRACE OUT THE CONTOUR FROM A START POINT
        SUBROUTINE TRACE
        COMMON/XYZ/IA2,IBUFF,JBUFF
        COMMON/ABC/IX1,IY1,ICOUNT,ISAVE(2000)
        BYTE IA2(256,256),IBUFF(256,256),JBUFF(256,256)
        ICOUNT=0
C       (IX1,IY1) IS THE START POINT INSIDE THE LIVER AND IS TRANFORMED TO MATRIX INDEX (ITRY,JTRY) HERE
        ITRY=IX1+129
        JTRY=128-IY1
555     CONTINUE
        JTRY=JTRY-1
C       TO TEST POINT (ITRY,JTRY) BEING A BOUNDARY POINT OR NOT
        CALL TEST(ITRY,JTRY,ITEST)
C       IF YES (ITEST=2), THEN START TO TRACE OUT THE CONTOUR
        IF(ITEST.EQ.2)THEN
        I1=ITRY
        J1=JTRY
        GO TO 101
        END IF
C       IF NO, THEN GO UP IN THE POSITIVE Y DIRECTION TO FIND ONE
        GO TO 555
777     CONTINUE
C       DRAW THE LINE BETWEEN TWO POINTS (I1,J1) AND (I2,J2)
        CALL DRAW(I1,J1,I2,J2)
```

```
C       IF THE SECOND POINT IS THE SAME AS THE BEGINNING POINT OF THE CONTOUR, THEN THE CONTOUR IS DONE AND CLOSED
        IF(I2.EQ.ITRY.AND.J2.EQ.JTRY)GO TO 888
        I21=I2-I1
        J21=J2-J1
C       NOW SHIFT TO THE NEW START POINT
        I1=I2
        J1=J2
C       AFTER TWO POINTS HAVE BEEN JOINED, THEN GO TO THE THIRD POINT TO TEST THAT IS IT A BOUNDARY POINT OR NOT
        IF(I21.EQ.1.AND.J21.EQ.0)GO TO 107
        IF(I21.EQ.1.AND.J21.EQ.-1)GO TO 107
        IF(I21.EQ.0.AND.J21.EQ.-1)GO TO 101
        IF(I21.EQ.-1.AND.J21.EQ.-1)GO TO 101
        IF(I21.EQ.-1.AND.J21.EQ.0)GO TO 103
        IF(I21.EQ.-1.AND.J21.EQ.1)GO TO 103
        IF(I21.EQ.0.AND.J21.EQ.1)GO TO 105
        IF(I21.EQ.1.AND.J21.EQ.1)GO TO 105
C       TRY THE EAST POINT TO BE A BOUNDARY POINT OR NOT? OTHERWISE SEARCH THE NEXT POINT IN ANTI-CLOCKWISE DIRECTION
101     CALL TEST(I1+1,J1,ITEST)
        IF(ITEST.EQ.2)THEN
        I2=I1+1
        J2=J1
        GO TO 777
        END IF
102     CALL TEST(I1+1,J1-1,ITEST)
        IF(ITEST.EQ.2)THEN
        I2=I1+1
        J2=J1-1
        GO TO 777
        END IF
103     CALL TEST(I1,J1-1,ITEST)
        IF(ITEST.EQ.2)THEN
        I2=I1
        J2=J1-1
        GO TO 777
        END IF
104     CALL TEST(I1-1,J1-1,ITEST)
        IF(ITEST.EQ.2)THEN
        I2=I1-1
        J2=J1-1
        GO TO 777
        END IF
105     CALL TEST(I1-1,J1,ITEST)
        IF(ITEST.EQ.2)THEN
        I2=I1-1
        J2=J1
        GO TO 777
        END IF
106     CALL TEST(I1-1,J1+1,ITEST)
        IF(ITEST.EQ.2)THEN
        I2=I1-1
        J2=J1+1
        GO TO 777
        END IF
107     CALL TEST(I1,J1+1,ITEST)
        IF(ITEST.EQ.2)THEN
        I2=I1
        J2=J1+1
        GO TO 777
        END IF
108     CALL TEST(I1+1,J1+1,ITEST)
        IF(ITEST.EQ.2)THEN
        I2=I1+1
        J2=J1+1
        GO TO 777
        END IF
        GO TO 101
888     RETURN
        END
C       THIS SUBROUTINE WAS WRITTEN TO TEST A POINT BEING A BOUNDARY POINT OR NOT
        SUBROUTINE TEST(MM,NN,ITEST)
        COMMON/XYZ/IA2,IBUFF,JBUFF
        COMMON/DEF/LOWER,UPPER
        BYTE IA2(256,256),IBUFF(256,256),JBUFF(256,256)
        BYTE LOWER,UPPER
        ITEST=0
C       IF THE PIXEL VALUE IS NOT WITHIN THE LOWER AND UPPER LIMITS, THEN IT IS NOT A BOUNDARY POINT
        IF(IA2(MM,NN).LT.LOWER.OR.IA2(MM,NN).GT.UPPER)GO TO 1111
C       THE END POINTS OF THE IMAGE MATRIX CANNOT BE BOUNDARY POINTS
        IF(MM.EQ.1.OR.MM.EQ.256)GO TO 1111
        IF(NN.EQ.1.OR.NN.EQ.256)GO TO 1111
        IIS=0
        IT1=0
        IT2=0
        IT3=0
        IT4=0
C       TEST THE 4 NEIGHBORING POINTS, ARE THEY WITHIN THE RANGE OF CT NUMBERS
C       IF THEY ARE NOT ALL "YES" OR "NO", THEN THE POINT IS A BOUNDARY POINT
        IF((IA2(MM+1,NN).GE.LOWER.AND.IA2(MM+1,NN).LE.UPPER)IT1=1
        IF((IA2(MM,NN-1).GE.LOWER.AND.IA2(MM,NN-1).LE.UPPER)IT2=1
        IF((IA2(MM-1,NN).GE.LOWER.AND.IA2(MM-1,NN).LE.UPPER)IT3=1
        IF((IA2(MM,NN+1).GE.LOWER.AND.IA2(MM,NN+1).LE.UPPER)IT4=1
        IIS=IT1+IT2+IT3+IT4
        IF(IIS.EQ.0.OR.IIS.EQ.4)GO TO 1111
C       ITEST=2 MEANS A BOUNDARY POINT, ITEST=0 MEANS NOT A BOUNDARY POINT
        ITEST=2
        JBUFF(MM,NN)=2
1111    CONTINUE
        RETURN
        END
C       THIS SUBROUTINE WAS WRITTEN TO CALCULATE THE VOLUME OF EACH SLICE IN TERMS OF THE TOTAL PIXEL NUMBER ON THAT SLICE
C       PLEASE SEE THE SUBROUTINE BLANK FOR EXPLANATION FOR MOST OF THE ALGORITHMS
        SUBROUTINE VOLUME(IVOL)
        COMMON/HIST/NHIS
        COMMON/ADC/IX1,IY1,ICOUNT,ISAVE(2000)
        COMMON/XYZ/IA2,IBUFF,JBUFF
        COMMON/MAXIN/IMIN,IMAX,JMIN,JMAX
        BYTE IA2(256,256),IBUFF(256,256),JBUFF(256,256)
        IVOL=0
        DO K=1,ICOUNT
        I=ISAVE(K)/1000
        J=MOD(ISAVE(K),1000)
        CALL IPARITY(K,IP)
        IBUFF(I,J)=IBUFF(I,J)+IP
        END DO
        DO J=JMIN,JMAX
        IFLAG=0
        IPAR=0
        DO I=IMIN,IMAX
```

```
         IF(IBUFF(I,J).EQ.1)THEN
         IFLAG=IFLAG+1
         IPAR=MOD(IFLAG,2)
         END IF
C        IPAR=1 MEANS THAT STARTING TO COUNT THE PIXELS INSIDE THE BOUNDARY
C        IPAR=0 AND IBUFF(I,J)=1 MEANS STARTING TO LEAVE THE REGION OF INTEREST BUT STILL ON THE BOUNDARY AND THAT POINT HAS TO BE
UNTED
C        IPAR=0 AND IBUFF(I,J)=10 MEANS A SINGULAR BOUNDARY POINT, AND SHOULD BE COUNTED
C        ONLY IPAR=0 AND IBUFF(I,J)=0 NEED NOT TO BE COUNTED
         IF(IPAR.EQ.0.AND.IBUFF(I,J).EQ.0)GO TO 99
         IVOL=IVOL+1
         FIA=IA2(I,J)
C        FILL THE HISTOGRAMS WITH THE PIXEL VALUES OF EQUAL WEIGHTS
         IF(NHIS.EQ.3)CALL HFI(1,FIA,1.)
         IF(NHIS.EQ.4)CALL HFI(2,FIA,1.)
99       CONTINUE
         IF(IBUFF(I,J).GT.0)IBUFF(I,J)=0
         END DO
         END DO
         RETURN
         END
C        THIS SUBROUTINE WAS WRITTEN TO BLANK THE DOWNWARD AREA OUTSIDE THE CONTOUR BETWEEN COLUMNS KX1 AND KX2
         SUBROUTINE BLKD(KX1,KX2)
         COMMON/XYZ/IA2,IBUFF,JBUFF
         INTEGER*2 KX1,KX2
         BYTE IA2(256,256),IBUFF(256,256),JBUFF(256,256)
         INTEGER*2 IBFLAG(256)
         DATA IBFLAG/256*0/
         IF(KX1.GT.KX2)THEN
         KTEM=KX1
         KX1=KX2
         KX2=KTEM
         END IF
         ISTART1=KX1+129
         ISTART2=KX2+129
         DO II=ISTART1,ISTART2
         DO JJ=1,256
         IF(JBUFF(II,JJ).EQ.2)IBFLAG(II)=JJ
         END DO
         IF(IBFLAG(II).NE.0)THEN
         IBLANK=IBFLAG(II)+1
         DO K=IBLANK,IBLANK+10
         IA2(II,K)=0
         END DO
         END IF
         IF(IBFLAG(II).EQ.0)THEN
         DO K=1,256
         IA2(II,K)=0
         END DO
         END IF
         END DO
         RETURN
         END
C        THIS SUBROUTINE WAS WRITTEN TO BLANK THE RIGHT-HAND SIDE AREA OUTSIDE THE CONTOUR BETWEEN ROWS KY1 AND KY2
         SUBROUTINE BLKR(KY1,KY2)
         COMMON/XYZ/IA2,IBUFF,JBUFF
         INTEGER*2 KY1,KY2
         BYTE IA2(256,256),IBUFF(256,256),JBUFF(256,256)
         INTEGER*2 JBFLAG(256)
         DATA JBFLAG/256*0/
         IF(KY2.GT.KY1)THEN
         JMM=KY1
         KY1=KY2
         KY2=JMM
         END IF
         JSTART1=128-KY1
         JSTART2=128-KY2
         DO JJ=JSTART1,JSTART2
         DO II=1,256
         IF(JBUFF(II,JJ).EQ.2)JBFLAG(JJ)=II
         END DO
         IF(JBFLAG(JJ).NE.0)THEN
         JBLANK=JBFLAG(JJ)+1
         DO K=JBLANK,JBLANK+10
         IA2(K,JJ)=0
         END DO
         END IF
         IF(JBFLAG(JJ).EQ.0)THEN
         DO K=1,256
         IA2(K,JJ)=0
         END DO
         END IF
         END DO
         RETURN
         END
C        THIS SUBROUTINE WAS WRITTEN TO BLANK THE UPWARD AREA OUTSIDE THE CONTOUR BETWEEN COLUMNS KX1 AND KX2
         SUBROUTINE BLKU(KX1,KX2)
         COMMON/XYZ/IA2,IBUFF,JBUFF
         INTEGER*2 KX1,KX2
         BYTE IA2(256,256),IBUFF(256,256),JBUFF(256,256)
         INTEGER*2 IBFLAG(256)
         DATA IBFLAG/256*0/
         IF(KX1.GT.KX2)THEN
         KX1=JTN
         KX1=KX2
         KX2=JTN
         END IF
         ISTART1=KX1+129
         ISTART2=KX2+129
         DO II=ISTART1,ISTART2
         DO JJ=256,1,-1
         IF(JBUFF(II,JJ).EQ.2)IBFLAG(II)=JJ
         END DO
         IF(IBFLAG(II).NE.0)THEN
         IBLANK=IBFLAG(II)-1
         DO K=IBLANK-10,IBLANK
         IA2(II,K)=0
         END DO
         END IF
         IF(IBFLAG(II).EQ.0)THEN
         DO K=1,256
         IA2(II,K)=0
         END DO
         END IF
         END DO
         RETURN
         END
```

```
C     THIS SUBROUTINE WAS WRITTEN TO BLANK THE LEFT-HAND SIDE AREA OUTSIDE THE CONTOUR BETWEEN ROWS KY1 AND KY2
      SUBROUTINE BLKL(KY1,KY2)
      COMMON/XYZ/IA2,IBUFF,JBUFF
      INTEGER*2 KY1,KY2
      BYTE IA2(256,256),IBUFF(256,256),JBUFF(256,256)
      INTEGER*2 JBFLAG(256)
      DATA JBFLAG/256*0/
      IF(KY2.GT.KY1)THEN
      JTEM=KY1
      KY1=KY2
      KY2=JTEM
      END IF
      JSTART1=128-KY1
      JSTART2=128-KY2
      DO JJ=JSTART1,JSTART2
      DO II=256,1,-1
      IF(JBUFF(II,JJ).EQ.2)JBFLAG(JJ)=II
      END DO
      IF(JBFLAG(JJ).NE.0)THEN
      JBLANK=JBFLAG(JJ)-1
      DO K=JBLANK-10,JBLANK
      IA2(K,JJ)=0
      END DO
      END IF
      IF(JBFLAG(JJ).EQ.0)THEN
      DO K=1,256
      IA2(K,JJ)=0
      END DO
      END IF
      END DO
      RETURN
      END
C     THIS SUBROUTINE WAS WRITTEN TO BLANK THE RIGHT-HAND SIDE AREA BETWEEN THE LINE SEGMENT FROM (KX1,KY1) TO (KX2,KY2)
      SUBROUTINE BLINER(KX1,KY1,KX2,KY2)
      COMMON/XYZ/IA2,IBUFF,JBUFF
      INTEGER*2 KX1,KY1,KX2,KY2
      BYTE IA2(256,256),IBUFF(256,256),JBUFF(256,256)
      IF(KY2.GT.KY1)THEN
      KTM=KY2
      KY2=KY1
      KY1=KTM
      JTM=KX2
      KX2=KX1
      KX1=JTM
      END IF
      IF(KY2.EQ.KY1)KY2=KY1-1
      J1=128-KY1
      J2=128-KY2
      CONT=FLOAT(KX2-KX1)/FLOAT(KY2-KY1)
      DO JJ=J1,J2
      KY=128-JJ
      KFACT=CONT*FLOAT(KY-KY1)
      KX=KX1+KFACT
      ISTART=KX+129
      DO II=ISTART,ISTART+10
      IA2(II,JJ)=0
      END DO
      END DO
      RETURN
      END
C     THIS SUBROUTINE WAS WRITTEN TO BLANK THE LEFT-HAND SIDE AREA BETWEEN THE LINE SEGMENT FROM (KX1,KY1) TO (KX2,KY2)
      SUBROUTINE BLINEL(KX1,KY1,KX2,KY2)
      COMMON/XYZ/IA2,IBUFF,JBUFF
      INTEGER*2 KX1,KY1,KX2,KY2
      BYTE IA2(256,256),IBUFF(256,256),JBUFF(256,256)
      IF(KY2.GT.KY1)THEN
      KTM=KY2
      KY2=KY1
      KY1=KTM
      JTM=KX2
      KX2=KX1
      KX1=JTM
      END IF
      IF(KY2.EQ.KY1)KY2=KY1-1
      J1=128-KY1
      J2=128-KY2
      CONT=FLOAT(KX2-KX1)/FLOAT(KY2-KY1)
      DO JJ=J1,J2
      KY=128-JJ
      KFACT=CONT*FLOAT(KY-KY1)
      KX=KX1+KFACT
      IEND=KX+129
      DO II=IEND-10,IEND
      IA2(II,JJ)=0
      END DO
      END DO
      RETURN
      END
C     THIS SUBROUTINE WAS WRITTEN TO BLANK THE DOWNWARD SIDE AREA BETWEEN THE LINE SEGMENT FROM (KX1,KY1) TO (KX2,KY2)
      SUBROUTINE BLINED(KX1,KY1,KX2,KY2)
      COMMON/XYZ/IA2,IBUFF,JBUFF
      INTEGER*2 KX1,KY1,KX2,KY2
      BYTE IA2(256,256),IBUFF(256,256),JBUFF(256,256)
      IF(KX1.GT.KX2)THEN
      KTEM=KX1
      KX1=KX2
      KX2=KTEM
      JTRM=KY1
      KY1=KY2
      KY2=JTRM
      END IF
      IF(KX1.EQ.KX2)KX1=KX2-1
      I1=129+KX1
      I2=129+KX2
      CONT=FLOAT(KY2-KY1)/FLOAT(KX2-KX1)
      DO II=I1,I2
      KX=II-129
      KFACT=CONT*FLOAT(KX-KX1)
      KY=KY1+KFACT
      JSTART=128-KY
      DO JJ=JSTART,JSTART+10
      IA2(II,JJ)=0
      END DO
      END DO
      RETURN
      END
C     THIS SUBROUTINE WAS WRITTEN TO BLANK THE UPWARD SIDE AREA BETWEEN THE LINE SEGMENT FROM (KX1,KY1) TO (KX2,KY2)
      SUBROUTINE BLINEU(KX1,KY1,KX2,KY2)
```

```
            COMMON/XYZ/IA2,IBUFF,JBUFF
            INTEGER*2 KX1,KY1,KX2,KY2
            BYTE IA2(256,256),IBUFF(256,256),JBUFF(256,256)
            IF(KX1.GT.KX2)THEN
            KTEM=KX1
            KX1=KX2
            KX2=KTEM
            JTRM=KY1
            KY1=KY2
            KY2=JTRM
            END IF
            IF(KX1.EQ.KX2)KX1=KX2-1
            I1=129+KX1
            I2=129+KX2
            CONT=FLOAT(KY2-KY1)/FLOAT(KX2-KX1)
            DO II=I1,I2
            KX=II-129
            KFACT=CONT*FLOAT(KX-KX1)
            KY=KY1+KFACT
            JEND=128-KY
            DO JJ=JEND-10,JEND
            IA2(II,JJ)=0
            END DO
            END DO
            RETURN
            END
C           THIS SUBROUTINE WAS WRITTEN TO BLANK A BAND AREA WITH BAND WIDTH (KX2-KX1) ON THE SPLINE BONE AREA
            SUBROUTINE BLKG(KX1,KX2)
            COMMON/XYZ/IA2,IBUFF,JBUFF
            INTEGER*2 KX1,KX2,IDIS
            BYTE IA2(256,256),IBUFF(256,256),JBUFF(256,256)
            IDIS=KX2-KX1
            DO 111 J=1,256
            IFLAG=0
            JFLAG=0
            DO 222 I=1,256
            IF(IFLAG.EQ.1.AND.JFLAG.EQ.1)GO TO 111
            IF(IFLAG.EQ.0.AND.IA2(I,J).GT.0)THEN
            DO K=0,IDIS
            IA2(I+K,J)=0
            END DO
            IFLAG=1
            END IF
            IF(JFLAG.EQ.0.AND.IA2(257-I,J).GT.0)THEN
C           DO K=0,IDIS
C           IA2(257-I-K,J)=0
C           END DO
            JFLAG=1
            END IF
222         CONTINUE
111         CONTINUE
            RETURN
            END
C           THIS PROGRAM WAS WRITTEN TO FILTER THE CT RAW DATA
C           BY A 5X5 LOW-PASS FILTER IT CAN FILTER ALL THE SLICES
C           IN ONE TIME. THE OUTPUT FORMAT OF EACH SLICE IS A 1600
C           CHARACTERS ID-BLOCK FOLLOWING BY A 256X256 BYTES
C           UNFORMATTED CT DATA
C           @ COPYRIGHT 1985,NAI-CHUEN YANG,PH.D. AND PETER K. LEICHNER,PH.D
            INTEGER*2 ITEM
            INTEGER*2 IA2(1024)
            CHARACTER*1 AB(2048),AC(1600)
            CHARACTER*19 NAME(60),MAME(60)
            CHARACTER*1 C1,C2,C3
            CHARACTER*2 NUM1
            CHARACTER*3 NUM
            CHARACTER*10 PATIENT
            CHARACTER*10 OUTPUT
            CHARACTER*11 CHAR3
            CHARACTER*15 CHAR1
            CHARACTER*16 CHAR2
            EQUIVALENCE (AB(1),IA2(1))
            INTEGER*2 IAR(256,256)
            BYTE IAB(256,256)
            TYPE *,'ENTER THE TAPE DATA SET NAME'
            READ(5,22)PATIENT
22          FORMAT(A10)
            TYPE *,'ENTER THE FIRST ,LAST NUMBERS IN TAPE'
            ACCEPT *,NBEG,NEND
            TYPE *,'ENTER THE OUTPUT PATIENT NAME'
            READ(5,22)OUTPUT
            TYPE *,'ENTER THE FIRST,LAST SCAN NUMBERS'
            ACCEPT *,NSCAN1,NSCAN2
            NTOT=NEND-NBEG+1
            DO 3 KK=1,NTOT
            TYPE *,KK
            CHAR1='MSA0:'//PATIENT
            CHAR2=CHAR1//'.'
            INUM=NBEG+KK-1
            I1=INUM/100
            I2=MOD(INUM,100)/10
            I3=MOD(MOD(INUM,100),10)
            C1=CHAR(I1+48)
            C2=CHAR(I2+48)
            C3=CHAR(I3+48)
            NUM1=C1//C2
            NUM=NUM1//C3
            NAME(KK)=CHAR2//NUM
            OPEN(UNIT=1,FILE=NAME(KK),STATUS='OLD',READONLY,SHARED,
           1    FORM='UNFORMATTED')
            NCOUNT=0
10          CONTINUE
            READ(1,END=999)IA2
            NCOUNT=NCOUNT+1
C           WRITE(6,100)NCOUNT
C           IF(NCOUNT.EQ.1)WRITE(6,101)(AB(K),K=1,64)
C           IF(NCOUNT.EQ.2)WRITE(6,101)(AB(K),K=513,2048)
            IF(NCOUNT.EQ.1)THEN
            DO K=1,64
            AC(K)=AB(K)
            END DO
            END IF
            IF(NCOUNT.EQ.2)THEN
            DO K=1,1536
            AC(K+64)=AB(K+512)
            END DO
            END IF
```

```
101         FORMAT(1X,16A1)
100         FORMAT(1X,8I10)
            IF(NCOUNT.GT.2)THEN
            NA1=4*(NCOUNT-2)-3
            NA2=NA1+1
            NA3=NA1+2
            NA4=NA1+3
            DO K=1,256
            IAR(K,NA1)=IA2(K)
            IAR(K,NA2)=IA2(K+256)
            IAR(K,NA3)=IA2(K+512)
            IAR(K,NA4)=IA2(K+768)
            END DO
            END IF
            GO TO 10
999         CONTINUE
            KSUM=0
            DO J=1,4
            DO I=1,4
            KSUM=KSUM+IAR(I,J)
            END DO
            END DO
            DO 111 J=1,252
            JP4=J+4
            KSUM=KSUM+IAR(1,JP4)+IAR(2,JP4)+IAR(3,JP4)+IAR(4,JP4)
            ISUM=KSUM
            KSUM=KSUM-IAR(1,J)-IAR(2,J)-IAR(3,J)-IAR(4,J)
            DO 222 I=1,252
            L=I+4
            ISUM=ISUM+IAR(L,J)+IAR(L,J+1)+IAR(L,J+2)+IAR(L,J+3)+IAR(L,J+4)
            ITEM=ISUM/25-1024
            IF(ITEM.LT.0)ITEM=0
            IF(ITEM.GT.127)ITEM=127
            IAB(I+2,J+2)=ITEM
            ISUM=ISUM-IAR(I,J)-IAR(I,J+1)-IAR(I,J+2)-IAR(I,J+3)-IAR(I,J+4)
222         CONTINUE
111         CONTINUE
            CHAR3=OUTPUT//'.'
            INUM=NBCAN1+KK-1
            I1=INUM/100
            I2=MOD(INUM,100)/10
            I3=MOD(MOD(INUM,100),10)
            C1=CHAR(I1+48)
            C2=CHAR(I2+48)
            C3=CHAR(I3+48)
            NUM1=C1//C2
            NUM=NUM1//C3
            MAME(KK)=CHAR3//NUM
            OPEN(UNIT=2,FILE=MAME(KK),STATUS='NEW',FORM='UNFORMATTED')
            WRITE(2)AC,IAB
            CLOSE(2)
3           CONTINUE
1000        STOP
            END
C           THIS PROGRAM WAS WRITTEN TO SET THE CONTRAST OF THE
C           CT IMAGES IN BLACK AND WHITE,GREY LEVELS RANGE FROM
C           0 TO 255.
C           @ COPYRIGHT 1985,NAI-CHUEN YANG,PH.D AND PETER K. LEICHNER,PH.D
            INTEGER*2 IB,LOWER,UPPER
            BYTE B
            CALL RTINIT( 'DMA', 3)
            CALL ENTGRA
            DO 10 J=0,255
            IB = J
            IF( IB .GT. 127 ) IB = IB - 256
            B=IB
            CALL LUT8(B,J,J,J)
10          CONTINUE
            CALL QUIT
50          CONTINUE
            TYPE *,'ENTER LOWER AND UPPER VALUES'
            ACCEPT *,LOWER,UPPER
            TYPE *,' LOWER =', LOWER, ' UPPER =', UPPER
            ILB=LOWER
            IUB=UPPER
            XM=255.0/FLOAT(IUB-ILB)
            CALL ENTGRA
            DO 20 J=0,255
            IB = J
            IF(IB GT 127)IB=IB-256
            B=IB
            IF(J LT ILB)THEN
            CALL LUT8( B, 0, 0, 0)
            END IF
            IF(J.GT.IUB)THEN
            CALL LUT8( B, 255, 255, 255 )
            END IF
            IF(J.GE.ILB AND.J.LE.IUB)THEN
            I=XM*FLOAT(J-ILB)
            CALL LUT8(B,I,I,I)
            END IF
20          CONTINUE
            CALL QUIT
            TYPE *,'ARE YOU SATISFIED ?,Y/N'
            READ(5,55)CSAT
55          FORMAT(A1)
            IF(CSAT.EQ.'Y')GO TO 999
            GO TO 50
999         CONTINUE
            STOP
            END
C           THIS PROGRAM WAS WRITTEN TO ADD THE HISTOGRAMS FROM
C           EVERY SLICE AND GET A GLOBAL HISTOGRAM
C           @ COPYRIGHT 1985,NAI-CHUEN YANG,PH.D AND PETER K. LEICHNER,PH.D
            COMMON//HB(100000)
            CHARACTER*2 NUM
            CHARACTER*15 CHAR1
            CHARACTER*1 C1,C2,C3
            CHARACTER*10 INPUT,OUTPUT
            CHARACTER*19 NAME(60),MAME(60)
            TYPE *,'ENTER THE FIRST AND LAST NUMBER OF THE HISTOGRAMS'
            ACCEPT *,NBEG,NEND
            TYPE *,'ENTER THE INPUT HISTOGRAM NAME'
            READ(5,15)INPUT
15          FORMAT(A10)
            NTOT=NEND-NBEG+1
            DO 3 KK=1,NTOT
            INUM=NBEG+KK-1
```

```
        I1=INUM/10
        I2=MOD(INUM,10)
        C1=CHAR(I1+48)
        C2=CHAR(I2+48)
        NUM=C1//C2
        CHAR1=INPUT//NUM
        NAME(KK)=CHAR1
        OPEN(UNIT=3,FILE=NAME(KK),STATUS='OLD',READONLY,SHARED,
     1    FORM='UNFORMATTED')
        CALL HFETCH(0,3)
3       CONTINUE
        TYPE *,'ENTER THE OUTPUT DATA SET NAME'
        READ(5,10)OUTPUT
10      FORMAT(A10)
        OPEN(UNIT=4,FILE=OUTPUT,STATUS='NEW',FORM='UNFORMATTED')
        CALL HSTORE(0,4)
1000    STOP
        END
C   THIS SUBPROGRAM WAS WRITTEN TO FIT THE GLOBAL HISTOGRAM
C   WITH THREE GAUSSIANS AND DETERMINE A TUMOR THRESHOLD .
C   AFTER THE THRESHOLD WAS DETERMINED , THE TOTAL LIVER AND
C   TUMOR VOLUMES WOULD BE CALCULATED.
C   @ COPYRIGHT 1985,NAI-CHUEN YANG,PH.D. AND PETER K. LEICHNER,PH.D
        FUNCTION USERFUN(X,Y)
        INCLUDE 'DISPLAY$LIBRARY:DISPLAY(USERFIT)'
        COMMON/HCFIT1/A,NITMAX,PREC
        DATA NITMAX/5000/
        TERM1=COEF(1)*EXP(-0.5*((X-COEF(2))/COEF(3))**2)
        TERM2=COEF(4)*EXP(-0.5*((X-COEF(5))/COEF(6))**2)
        TERM3=COEF(7)*EXP(-0.5*((X-COEF(8))/COEF(9))**2)
        USERFUN=TERM1+TERM2+TERM3
        END
        Subroutine HIFius
        Include 'Display$library:Display(HPLOU)'
        Include 'Display$library:Display(Userfit)'
        DATA ST/50.,1.,0.1,50.,1.,0.1,50.,1.,0.1,11*1./
        DATA PMI/5000.,35.,2.,500.,25.,2.,50.,0.2.,11*2./
        DATA PMX/95000.,125.,4.,10000.,65.,5,5000.,55.,5.,11*1./
        DATA COEF/10000.,45.,3.5,1000.,35.,3.5,100.,25,3.5,11*1./
        External Userfun
        CALL HLALPHA
        IFLAG=0
        If (Icou.Eq.0) Then
           Iflerr = 2
           Return
        End If
        If (Idim(Icou).Ne 1) Then
           Iflerr = 7
           Return
        End If
        Id=Iv(Icou)
        TYPE *,'IS IT THE FIRST TIME TO FIT,Y/N?'
        READ(5,55)CF
55      FORMAT(A2)
        IF(CF.EQ.'N')GO TO 9
        Amax=Hmax(ID)
        DO KX=1,100
        FX=KX
        VAL=HX(ID,FX)
        VAM=0.25*AMAX
        VAMM=0.05*AMAX
        VAU=HX(ID,FX+1 )
        IF(VAL.LE.VAMM.AND.VAU.GE.VAMM)THEN
        PMI(7)=VAMM-0.3*VAMM
        PMX(7)=VAMM+0.3*VAMM
        COEF(7)=VAMM
        PMI(8)=FX-5.
        PMX(8)=FX+5.
        COEF(8)=FX
        F2=FX
        END IF
        IF(VAL.LE.VAM.AND.VAU.GE.VAM)THEN
C       TYPE *,'I FOUND THE 0.25*MAX=',VAM,VAL,VAU,'AT CT#=',FX
        PMI(4)=VAM-0.3*VAK
        PMX(4)=VAM+0.3*VAM
        COEF(4)=VAM
        PMI(5)=FX-3.
        PMX(5)=FX+3.
        COEF(5)=FX
        F1=FX
        END IF
        IF(VAL.EQ.AMAX)THEN
        VALL=HX(ID,FX-1.)
C       TYPE *,'I FOUND THE MAX=',AMAX,VALL,VAU,'AT CT# = ',FX
        PMI(1)=VAL-VAL*0.1
        PMX(1)=VAL+VAL*0.1
        COEF(1)=VAL
        PMI(2)=FX-1.
        PMX(2)=FX+1.
        COEF(2)=FX
        F0=FX
        END IF
        IF(VAL.GE.VAM.AND.VAU.LE.VAM)THEN
C       TYPE *,'I FOUND ANOTHER 0.25*MAX=',VAM,VAL,VAU ,'AT CT#=',FX+1.
        F11=FX+1.
        IF((FX+1.-F0).GT.(F0-F1))THEN
        IFLAG=1
        TYPE *,'THIS PERSON LOOKS LIKE A LARGE TUMOR PATIENT'
        PMI(5)=FX+1.-2.
        PMX(5)=FX+1 +2
        COEF(5)=FX+1
        TYPE *,'DO YOU AGREE,Y/N?'
        READ(5,55)CL
        IF(CL.EQ.'N')THEN
        TYPE *,'NOW TREAT THE PATIENT AS A SMALL TUMOR PATIENT'
        PMI(5)=F1-2.
        PMX(5)=F1+2.
        COEF(5)=F1
        END IF
        END IF
        END IF
        END DO
        IF(IFLAG.EQ.0)THEN
        TYPE *,'THIS PERSON LOOKS LIKE A SMALL TUMOR PATIENT'
        TYPE *,'DO YOU AGREE,Y/N?'
        READ(5,55)CK
        IF(CK.EQ.'N')THEN
        TYPE *,'NOW TREAT THE PATIENT AS A LARGE TUMOR PATIENT'
```

```
            PMI(5)=F11-2.
            PMX(5)=F11+2.
            COEF(5)=F11
            END IF
            END IF
9           TYPE *,'DO YOU WANT TO ADJUST THE PARAMETERS, Y/N?'
            READ(5,55)AFIT
            IF(AFIT.EQ.'N')GO TO 10
            TYPE *,'WHICH GAUSSIAN YOU WANT TO ADJUST ,1,2,OR 3?'
            ACCEPT *,KK
            IF(KK.GT.3)KK=3
            TYPE *,'ENTER THE COEFS AND THE LOWER AND UPPER LIMITS'
            READ(5,*)COEF(3*KK-2),PMI(3*KK-2),PMX(3*KK-2)
            READ(5,*)COEF(3*KK-1),PMI(3*KK-1),PMX(3*KK-1)
            READ(5,*)COEF(3*KK),PMI(3*KK),PMX(3*KK)
            CALL HLALPHA
            DO K=1,9
            TYPE *,COEF(K),PMI(K),PMX(K)
            IF(MOD(K,3).EQ.0)TYPE *,' '
            END DO
            GO TO 9
10          CONTINUE
            Np=9
            Ic=2
            TYPE *,'NOW START TO FIT,PLEASE BE PATIENT'
11          Call Hfit(ID,Userfun,Np,Coef,Chi2,Ic,Sig,Cov,St,Pmi,Pmx)
            CALL HLPLOT(1)
            TYPE *,'DO YOU WANT TO TRY AGAIN,Y/N?'
            READ(5,55)CTT
            IF(CTT.EQ.'N')GO TO 999
            CALL HLALPHA
            CALL HXI(ID,F0,I0)
            VALF=HIF(ID,I0)
            DVAL=VALF-AMAX
            PVAL=DVAL/AMAX
            TYPE *,'MAX DIFF=',DVAL,'PER CENT MAX DIFF=',PVAL
            COFF(1)=COEF(1)-DVAL
            IF(DVAL.LT.0.0)THEN
            PMI(1)=COEF(1)
            PMX(1)=COEF(1)+0.1*COEF(1)
            END IF
            IF(DVAL.GT.0.0)THEN
            PMI(1)=COEF(1)-0.1*COEF(1)
            PMX(1)=COEF(1)
            END IF
            GO TO 11
999         CF='N'
            RETURN
            END
            Subroutine Hlprus
            Include 'Display$library:Display(HPLOU)'
            Include 'Display$library:Display(userfit)'
            Common /Htaplo/ Iout
            Dimension Itit(22)
            If (Id.Eq.0) Then
               Type *,'No user fit done'
               Call Linrd(1,1)
               Return
            End If
            Call Hargul(Id,Itit,Nc,Dv,Fv)
            Ntit=Itit(1)+1
            Call Hlalpha
            Write(6,1000) Id,(Itit(K),K=2,Ntit)
            If (Iout.Ne.6) Write(Iout,1002) Id,(Itit(K),K=2,Ntit)
1000        Format(5X,I5,1X,19A4)
1002        Format('1'/5X,I5,1X,19A4)
            Write(6,1001)Np,Chi2
            If (Iout.Ne.6) Write(Iout,1001)Np,Chi2
1001        Format(5X' User fit. parameters=',I3,' chi2= ',E12.5)
            Write(6,1004)(Coef(K),K=1,Np)
            If (Iout.Ne.6) Write(Iout,1004)(Coef(K),K=1,Np)
1004        Format(5X' coefficients: ',3F13.5/(19X3F13.5))
            Write(6,1003)(Sig(K),K=1,Np)
            If (Iout.Ne.6) Write(Iout,1003)(Sig(K),K=1,Np)
1003        Format(5X' their sigmas: ',3F13.5/(19X3F13.5))
            CALL INTRD('ENTER 0 FOR SMALL,1 FOR LARGE TUMOR',ISL)
            IF(ISL.EQ.0)THEN
            TH1=COEF(2)-1.6651*COEF(3)-1
            IF(COEF(2).GT.66.)TH1=-3.3+.86*COEF(2)
            END IF
            IF(ISL.EQ.1)THEN
            TH1=COEF(2)+0.75853*COEF(3)
            END IF
            TYPE *,'HERE IS THE TUMOR THRESHOLD'
            TYPE *,TH1
            CALL HNOENT(ID,NTOTAL)
            ITH=TH1
            FTH=ITH
            DTH=TH1-FTH
            IF(DTH.GE.0.5)ITH=ITH+1
            VALX=0.0
            DO KX=16,ITH
            GX=KX
            VALX=VALX+HX(ID,GX)
            END DO
            CALL FLTRD('PLEASE ENTER ZOOM FACTOR',ZOOM)
            IF(ZOOM.EQ.1.5)VOXEL=0.0168028
            IF(ZOOM.EQ.1.6)VOXEL=0.014768085
            IF(ZOOM.EQ.1.70)VOXEL=0.014786464
            IF(ZOOM.EQ.1.71)VOXEL=0.013149053
            IF(ZOOM.GT.1.71.OR.ZOOM.LT.1.5)THEN
            VOXEL=0.0168028*(1.5/ZOOM)**2
            END IF
            NTUMOR=VALX
            PIXEL=VOXEL/0.8
            WRITE(6,111)VOXEL
111         FORMAT(1X,'VOXEL SIZE= ',F10.8,' CC')
            WRITE(6,112)PIXEL
112         FORMAT(1X,'PIXEL SIZE= ',F10.8,' CM**2')
            TYPE *,'TOTAL COUNT=',NTOTAL
            TYPE *,'TUMOR COUNT=',NTUMOR
            VOL=VOXEL*NTUMOR
            TVOL=VOL*NTOTAL/NTUMOR
            TYPE *,'TOTAL VOLUME=',TVOL,'CC'
            TYPE *,'TUMOR VOLUME=',VOL,'CC'
            Return
            End
            Subroutine Hlblow(Iku)
```

```
          Include 'Display$library:Display(HPLOU)'
          Common /Poubel/ C(Nb1n2),Cu(Nb1n2)
          Dimension Itit(22)
          If (Icou.Eq.0) Then
             Iflerr = 2
             Return
          End If
          Ide=Iv(Icou)
          Call Hnoent(Ide,Noent)
          NTOTAL=NOENT
          Call Hifnid(Ids,Ide)
          Call Hiinsr(Ids,Idim(Icou))
          If(Idim(Icou).Eq.2) Go To 200
          Call Hargu1(Ide,Itit,Nch,Dv,Fv)
    C     Call Himoti('BLO ',Itit)
          Call Hunpak(Ide,C,Choice,1)
          Cu1 = Hie(Ide,1)
          IF (Cu1.Ge.0) Then
             Ipake = 1
             Do I = 1,Nch
                Cu(I) = Hie(Ide,1)
             End Do
          Else
             Ipake = 0
          End If
          Bsz=(Fv-Dv)/Nch If(Iku.Eq.1)Go To 222
          Ali = Dv
          Als = Fv
          Call Fltrd('Lower limit',Ali,Dv,Fv)
          Call Fltrd('Upper limit',Als,Ali,Fv)
          Icd=(Ali-Dv)/Bsz
          Icf=(Als+1.-Dv+.99*Bsz)/Bsz
          Go To 223
    222   Continue
          Do 30 Icd=1,Nch
          If(C(Icd).Ne.0.) Go To 31
    30    Continue
          Icd=Nch
    31    Continue
          Icd=Icd-1
          Icf=Nch
          Do 32 Ioc=1,Nch
          If(C(Icf).Ne.0.) Go To 33
          Icf=Icf-1
    32    Continue
    33    Continue
          If(Icd.Ge.Icf) Then
             Iflerr = 8
             Return
          End If
    223   Continue
          Ali=Icd*Bsz+Dv
          Als=Icf*Bsz+Dv
          Ncn=Icf-Icd
          Ipd=Jmax0(0,Icd)
          Iad=Jmax0(0,-Icd)
          Ncf=Jmin0(Nch,Icf)-Ipd
          Iaf=Iad+Ncf
          Call Hbook1(Ids,Itit,Ncn,Ali,Als,0.)
          Call Hpak(Ids,C(Ipd+1))
    C     If (Ipake.Ne.0) Call Hpake(Ids,Cu(Ipd+1))
          Temp = Hsum(Ids)
          Noent = Int(Temp)
          Call Hient(Ids,Noent)
          CALL FLTRD('PLEASE ENTER ZOOM FACTOR',ZOOM)
          IF(ZOOM.EQ.1.5)VOXEL=0.0168028
          IF(ZOOM.EQ.1.6)VOXEL=0.014768085
          IF(ZOOM.EQ.1.70)VOXEL=0.014786464
          IF(ZOOM.EQ.1.71)VOXEL=0.013149053
          IF(ZOOM.GT.1.71.OR.ZOOM.LT.1.5)THEN
          VOXEL=0.0168028*(1.5/ZOOM)**2
          END IF
          PIXEL=VOXEL/0.8
          WRITE(6,111)VOXEL
    111   FORMAT(1X,'VOXEL SIZE=  ',F10.8,' CC')
          WRITE(6,112)PIXEL
    112   FORMAT(1X,'PIXEL SIZE=  ',F10.8,' CM**2')
          TYPE *,'TOTAL COUNT=',NTOTAL
          TYPE *,'TUMOR COUNT=',NOENT
          VOL=VOXEL*NOENT
          TVOL=VOL*NTOTAL/NOENT
          TYPE *,'TOTAL VOLUME=',TVOL,'CC'
          TYPE *,'TUMOR VOLUME=',VOL,'CC'
          Return
    200   Continue
          Call Hargu2(Ide,Itit,Nx,Dx,Fx,Ny,Dy,Fy)
    C     Call Himoti('BLO ',Itit)
          Xli = Dx
          Xls = Fx
          Yli = Dy
          Yls = Fy
          Call Fltrd('X lower limit',Xli,Dx,Fx)
          Call Fltrd('X upper limit',Xls,Xli,Fx)
          Call Fltrd('Y lower limit',Yli,Dy,Fy)
          Call Fltrd('Y upper limit',Yls,Yli,Fy)
          Bszx=(Fx-Dx)/Nx
          Icdx=(Xli-Dx)/Bszx
          Xli=Icdx*Bszx+Dx
          Icfx=(Xls-Dx+.99*Bszx)/Bszx
          Xls=Icfx*Bszx+Dx
          Nnx=Icfx-Icdx
          Bszy=(Fy-Dy)/Ny
          Icdy=(Yli-Dy)/Bszy
          Yli=Icdy*Bszy+Dy
          Icfy=(Yls-Dy+.99*Bszy)/Bszy
          Yls=Icfy*Bszy+Dy
          Nny=Icfy-Icdy
          Call Hbook2(Ids,Itit,Nnx,Xli,Xls,Nny,Yli,Yls,8)
          Call Hunpak(Ide,C,'HIST',1)
          Do 203 Iy=1,Nny
          Do 203 Ix=1,Nnx
          Ixy=(Iy-1)*Nnx+Ix
          Jxy=(Iy+Icdy-1)*Nx+Ix+Icdx
          Cu(Ixy)=C(Jxy)
```

```
203     Continue
        Call Hpak(Ids,Cu)
        Temp = Hsum(Ids)
        Noent = Int(Temp)
        Call Hlent(Ids,Noent)
        End
C       THIS PROGRAM WAS WRITTEN TO HIGHLIGHT THE CT SLICES
C       WITH TWO COLORS FOR THE LIVER THE PINK COLOR REPRESENTS
C       THE NORMAL LIVER,WHILE THE YELLOW COLOR REPRESENTS THE
C       TUMOR.
C       @ COPYRIGHT 1985,NAI-CHUEN YANG,PH.D. AND PETER K. LEICHNER,PH.D
        COMMON/XYZ/IAB,JBUFF
        COMMON/ABC/JCOUNT,JSAVE(2000)
        COMMON/GHI/IBK,IBNK
        COMMON/MAXIN/IMIN,IMAX,JMIN,JMAX
        CHARACTER*1 AB(1600)
        CHARACTER*1 IBK,IBNK
        CHARACTER*30 NAME
        INTEGER*2 LOWER,UPPER
        INTEGER*2 ICONL,ICONH
        BYTE IAB(256,256),JBUFF(256,256)
        CALL RTINIT('DMA',3)
3       CONTINUE
        WRITE(6,2)
2       FORMAT(X,'ENTER THE DATASET NAME,OR ENTER DONE TO QUIT')
        READ(5,1)NAME
1       FORMAT(A30)
        IF(NAME.EQ.'DONE')GO TO 1000
        OPEN(UNIT=80,FILE=NAME,STATUS='OLD',READONLY,SHARED,
     1       FORM='UNFORMATTED')
        READ(80)AB,IAB
C       WRITE(6,101)(AB(K),K=1,1600)
101     FORMAT(1X,16A1)
        CALL ENTGRA
        CALL MOVABS(-128,255)
        CALL PIXEL8(256,256,IAB)
        CALL QUIT
22      TYPE *,'ENTER THE CONTRAST VALUES'
        ACCEPT *,ICONL,ICONH
        CALL CONTRAST1(ICONL,ICONH)
        TYPE *,'ARE YOU SATISFIED? ,Y OR N?'
        READ(5,55)SATI
55      FORMAT(A1)
        IF(SATI.EQ.'Y')GO TO 12
        GO TO 22
12      CONTINUE
        CALL LAST
        CALL BLTEST(IBNK)
        CALL CONTRAST2(ICONL,ICONH)
        CALL BLANK
        DO JJ=JMIN,JMAX
        DO II=IMIN,IMAX
        IAB(II,JJ)=IAB(II,JJ)-128
        END DO
        END DO
        CALL ENTGRA
        CALL MOVABS(-128,-1)
        CALL PIXEL8(256,256,IAB)
        CALL QUIT
        KCOUNT=0
13      KCOUNT=KCOUNT+1
        TYPE *,'ENTER THE LOWER AND UPPER LIMITS OF TUMOR'
        ACCEPT *,LOWER,UPPER
        IF(LOWER.EQ.127)GO TO 1000
        TYPE *,'ENTER W FOR WHOLE,N FOR NORMAL,T FOR TUMOR'
        READ(5,17)IBK
17      FORMAT(A1)
        CALL COLOUR(LOWER,UPPER)
        IF(KCOUNT.GT.1)GO TO 13
        DO 500 KK=1,JCOUNT
        II=JSAVE(KK)/1000
        JJ=MOD(JSAVE(KK),1000)
        IF(KK.NE.JCOUNT)THEN
        MM=JSAVE(KK+1)/1000
        NN=MOD(JSAVE(KK+1),1000)
        END IF
        IF(KK.EQ.JCOUNT)THEN
        MM=JSAVE(1)/1000
        NN=MOD(JSAVE(1),1000)
        END IF
        CALL DRAW2(II,JJ,MM,NN)
500     CONTINUE
        GO TO 13
1000    CONTINUE
999     STOP
        END
        SUBROUTINE CONTRAST1(LOW,HIGH)
        INTEGER*2 LOW,HIGH
        BYTE B
        TYPE *,' LOW =',LOW,' HIGH =',HIGH
        XM=255.0/FLOAT(HIGH-LOW)
        CALL ENTGRA
        DO 20 JJ=0,127
        B=JJ
        IF(JJ.LT.LOW)THEN
        CALL LUT8( B, 0, 0, 0)
        END IF
        IF(JJ.GT.HIGH)THEN
        CALL LUT8( B, 255, 255, 255 )
        END IF
        IF(JJ.GE.LOW.AND.JJ.LE.HIGH)THEN
        I=XM*FLOAT(JJ-LOW)
        CALL LUT8(B,I,I,I)
        END IF
20      CONTINUE
        CALL QUIT
        RETURN
        END
        SUBROUTINE CONTRAST2(LOW,HIGH)
        INTEGER*2 LOW,HIGH
        BYTE B
        LOW=LOW-128
        HIGH=HIGH-128
        XM=255.0/FLOAT(HIGH-LOW)
        CALL ENTGRA
        DO 20 JJ=-128,-1
        B=JJ
```

```
           IF(JJ.LT.LOW)THEN
           CALL LUT8( B, 0, 0, 0)
           END IF
           IF(JJ.GT.HIGH)THEN
           CALL LUT8( B, 255, 255, 255 )
           END IF
           IF(JJ.GE.LOW AND JJ.LE.HIGH)THEN
           I=XM*FLOAT(JJ-LOW)
           CALL LUT8(B,I,I,I)
           END IF
  20       CONTINUE
           CALL QUIT
           RETURN
           END
           SUBROUTINE COLOUR(BOTTOM,TOP)
           COMMON/GHI/IBK,IBNK
           CHARACTER*1 IBK,IBNK
           INTEGER*2 BOTTOM,TOP
           BYTE B
           BOTTOM=BOTTOM-128
           TOP=TOP-128
           CALL ENTGRA
           DO 20 JJ=-128,-2
           B=JJ
           IF(JJ.LT.BOTTOM)CALL LUT8(B,0,0,0)
           IF(JJ.GE.BOTTOM.AND.JJ.LE.TOP)THEN
           IF(IBK.EQ.'N')CALL LUT8(B,0,0,0)
           IF(IBK.EQ.'W'.OR.IBK.EQ.'T')THEN
           IRED=255
           IGRN=150
           IBLU=0
           CALL LUT8(B,IRED,IGRN,IBLU)
           END IF
           END IF
           IF(JJ.GT.TOP)THEN
           IF(IBK.EQ.'T')CALL LUT8(B,0,0,0)
           IF(IBK.EQ.'W'.OR.IBK.EQ.'N')THEN
           IRED=255
           IGRN=75
           IBLU=125
           CALL LUT8(B,IRED,IGRN,IBLU)
           END IF
           END IF
  20       CONTINUE
           CALL QUIT
           RETURN
           END
           SUBROUTINE LAST
           COMMON/ABC/JCOUNT,JSAVE(2000)
           COMMON/GHI/IBK,IBNK
           COMMON/XYZ/IAB,JBUFF
           COMMON/MAXIN/IMIN,IMAX,JMIN,JMAX
           BYTE IAB(256,256),JBUFF(256,256)
           CHARACTER*30 MAME
           CHARACTER*1 IBK,IBNK
           TYPE *,'ENTER THE BOUNDARY'
           READ(5,2)MAME
  2        FORMAT(A30)
           OPEN(UNIT=2,FILE=MAME,STATUS='OLD',READONLY,SHARED,
     1     FORM='UNFORMATTED')
           READ(2)JCOUNT,(JSAVE(KK),KK=1,JCOUNT)
           IMIN=JSAVE(1)/1000
           IMAX=IMIN
           JMIN=MOD(JSAVE(1),1000)
           JMAX=JMIN
           DO 5000 KK=1,JCOUNT
           II=JSAVE(KK)/1000
           JJ=MOD(JSAVE(KK),1000)
           IF(II.LT.IMIN)IMIN=II
           IF(II.GT.IMAX)IMAX=II
           IF(JJ.LT.JMIN)JMIN=JJ
           IF(JJ.GT.JMAX)JMAX=JJ
           IF(KK.NE.JCOUNT)THEN
           MM=JSAVE(KK+1)/1000
           NN=MOD(JSAVE(KK+1),1000)
           END IF
           IF(KK.EQ.JCOUNT)THEN
           MM=JSAVE(1)/1000
           NN=MOD(JSAVE(1),1000)
           END IF
           CALL DRAW1(II,JJ,MM,NN)
  5000     CONTINUE
           RETURN
           END
           SUBROUTINE DRAW1(II,JJ,MM,NN)
           COMMON/GHI/IBK,IBNK
           CHARACTER*1 IBK,IBNK
           IXO=II-129
           IYO=256-JJ
           IX=MM-129
           IY=256-NN
           CALL ENTGRA
           CALL MOVABS(IXO,IYO)
           CALL VALUE(0,255,0)
           CALL DRWABS(IX,IY)
           CALL QUIT
           RETURN
           END
           SUBROUTINE DRAW2(II,JJ,MM,NN)
           COMMON/GHI/IBK,IBNK
           CHARACTER*1 IBK,IBNK
           IXO=II-129
           IYO=-JJ
           IX=MM-129
           IY=-NN
           CALL ENTGRA
           CALL MOVABS(IXO,IYO)
           CALL VALUE(0,255,0)
           CALL DRWABS(IX,IY)
           CALL QUIT
           RETURN
           END
           SUBROUTINE BLANK
           COMMON/ABC/JCOUNT,JSAVE(2000)
           COMMON/XYZ/IAB,JBUFF
           BYTE IAB(256,256),JBUFF(256,256)
           DO K=1,JCOUNT
           I=JSAVE(K)/1000
```

```
J=MOD(JSAVE(K),1000)
CALL TPARITY(K,IP)
JBUFF(I,J)=JBUFF(I,J)+IP
END DO
DO JJ=1,256
IFLAG=0
IPAR=0
DO II=1,256
IF(JBUFF(II,JJ).EQ.1)THEN
IFLAG=IFLAG+1
IPAR=MOD(IFLAG,2)
END IF
IF((IPAR.EQ.0.AND.JBUFF(II,JJ).EQ.0)THEN
IAR(II,JJ)=0
END IF
END DO
END DO
END DO
RETURN
END
SUBROUTINE TPARITY(NUM,IPARITY)
COMMON/ABC/JCOUNT,JSAVE(2000)
COMMON/GHI/IBK,IBNK
CHARACTER*1 IBK,IBNK
NUM1=NUM-1
NUM2=NUM+1
IF(NUM.EQ.1)NUM1=JCOUNT
IF(NUM.EQ.JCOUNT)NUM2=1
I=JSAVE(NUM)/1000
J=MOD(JSAVE(NUM),1000)
I1=JSAVE(NUM1)/1000
J1=MOD(JSAVE(NUM1),1000)
I2=JSAVE(NUM2)/1000
J2=MOD(JSAVE(NUM2),1000)
IPARITY=1
LI2=I2-I
LI1=I-I1
LJ2=J2-J
LJ1=J-J1
IF(J2.EQ.J1)IPARITY=10
IF(IBNK.EQ.'C')THEN
IF(LJ1.EQ.0.AND.LJ2.EQ.-1.AND.LI1.EQ.1)IPARITY=0
IF(LJ1.EQ.1.AND.LJ2.EQ.0.AND.LI2.EQ.1)IPARITY=0
IF(LJ1.EQ.0.AND.LJ2.EQ.1.AND.LI1.EQ.-1)IPARITY=0
IF(LJ1.EQ.-1.AND.LJ2.EQ.0.AND.LI2.EQ.-1)IPARITY=0
END IF
IF(IBNK.EQ.'A')THEN
IF(LJ1.EQ.1.AND.LJ2.EQ.0.AND.LI2.EQ.-1)IPARITY=0
IF(LJ1.EQ.0.AND.LJ2.EQ.-1.AND.LI1.EQ.-1)IPARITY=0
IF(LJ1.EQ.-1.AND.LJ2.EQ.0.AND.LI2.EQ.1)IPARITY=0
IF(LJ1.EQ.0.AND.LJ2.EQ.1.AND.LI1.EQ.1)IPARITY=0
END IF
RETURN
END
SUBROUTINE DLTEST(KBLANK)
COMMON/ABC/JCOUNT,JSAVE(2000)
INTEGER*2 II(30),JJ(30)
CHARACTER*1 KBLANK
DO L=1,30
II(L)=JSAVE(L)/1000
JJ(L)=MOD(JSAVE(L),1000)
END DO
IFIRST=1
9   CONTINUE
IUP=0
IDOWN=0
DO K=IFIRST+1,JCOUNT
I=JSAVE(K)/1000
J=MOD(JSAVE(K),1000)
IF(I.EQ.II(IFIRST).AND.J.LT.JJ(IFIRST))IUP=IUP+1
IF(I.EQ.II(IFIRST).AND.J.GT.JJ(IFIRST))IDOWN=IDOWN+1
END DO
MU=MOD(IUP,2)
MD=MOD(IDOWN,2)
IF(MD.EQ.MU)THEN
IFIRST=IFIRST+1
GO TO 9
END IF
IF(MU.EQ.1.AND.MD.EQ.0.AND.II(IFIRST).GT.II(IFIRST+1))KBLANK='C'
IF(MU.EQ.0.AND.MD.EQ.1.AND.II(IFIRST).LT.II(IFIRST+1))KBLANK='C'
IF(MU.EQ.1.AND.MD.EQ.0.AND.II(IFIRST).LT.II(IFIRST+1))KBLANK='A'
IF(MU.EQ.0.AND.MD.EQ.1.AND.II(IFIRST).GT.II(IFIRST+1))KBLANK='A'
IF(KBLANK.EQ.'C')TYPE *,'THIS IS A CLOCKWISE CONTOUR'
IF(KBLANK.EQ.'A')TYPE *,'THIS IS AN ANTI-CLOCKWISE CONTOUR'
RETURN
END
```

1. A computer-aided method for determining the volume of a tumor within a body organ from CT image data of that organ, comprising the steps of:

(a) obtaining CT image data for each of a plurality of slices of predetermined thickness of the body organ, the image data including a plurality of pixels and a CT number corresponding to each pixel;

(b) transferring the CT image data into a computer;

(c) displaying from the data in the computer an image of one of the slices;

(d) computer generating an approximate boundary of the organ and displaying the boundary superimposed on the image of the slice;

(e) operator interacting with the computer to modify the boundary generated by the computer to more accurately describe the boundary of the organ;

(f) identifying, by the computer, the particular pixels within the organ boundary and the CT number associated with each such pixel and generating therefrom a local histogram of the slice, the histogram including data indicative of the number of pixels within the boundary having a particular CT number;

(g) from the predetermined thickness and number of pixels identified within the boundary, determining by the computer, the volume of organ within the slice;

(h) repeating steps (c) through (g) for each slice to so as to determine a local histogram corresponding to each slice;

(i) summing the local histograms corresponding to the various slices to obtain a global histogram indicative of the number of pixels within the orga boundaries of respective slices having each particular CT number;

(j) determining from the global histogram a demarcation CT number that distinguishes between normal organ tissue and tumor;

(k) determining from the volume computations for each of the slices, the total volume of the organ; and (l) computing from the global histogram and demarcation CT number, the volume of the tumor.

2. A method according to claim 1 wherein step (d) comprises the steps of:

(1) operator specifying a CT number threshold criteria for defining the boundary of the organ;

(2) operator specifying a seed pixel by visually ascertaining an arbitrary point within the organ;

(3) beginning at the seed pixel, searching from one pixel to the next to locate a first boundary pixel meeting the threshold criteria specified;

(4) examining nearest neighboring pixels to the first boundary pixel to determine if they meet the threshold criteria to find a second boundary pixel, (5) drawing a vector from the first boundary pixel to the second boundary pixel, (6) examining pixels neighboring to said second boundary pixel to determine third, fourth, . . . nth boundary pixels and drawing vectors from each last found pixel to a newly found pixel, to generate a series of vectors defining the boundary of the organ.

3. A method according to claim 1 wherein step (d) comprises the step of reading data defining the boundary determined for a previously boundary defined slice and utilizing that previously determined boundary for the current slice.

4. A method according to claim 1 wherein step (j) comprises the step of the operator visually examining the global histogram and selecting the demarcation CT number based on predetermined criteria.

5. A method according to claim 1 wherein step (j) comprises the step of the computer fitting the global histogram to a sum of three gaussian functions given by $$F(n) = \sum_{i=1}^{3} A_i \exp\left[ -\frac{(n - n_i)^2}{2\sigma_i^2} \right]. \quad (1)$$

wherein n represents the CT numbers and $n_i$ their mean value for each of the Gaussian functions, $A_i$ and $\sigma_i^2$ are the corresponding amplitude, and variance, respectively.

6. A computer-based arrangement for determining the volume of a tumor within a body organ from CT image data of that organ, comprising:

(a) means for obtaining CT image data for each of a plurality of slices of predetermined thickness of the body organ, the image data including a plurality of pixels and a CT number corresponding to each pixel;

(b) means for reading the CT image data;

(c) means for displaying one at a time, an image of each slice;

(d) means for generating, for each slice, an approximate boundary of the organ and displaying the boundary superimposed on the image of the slice;

(e) means for operator interacting with said arrangement to modify the boundary generated and displayed for each slice to ore accurately describe the boundary of the organ;

(f) means of identifying, for each slice, the particular pixels within the organ boundary and the CT number associated with each such pixel and generating therefrom a local histogram of the slice, the histogram including data indicative of the number of pixels within the boundary having a particular CT number;

(g) means for determining, for each slice, from the predetermined thickness and number of pixels identified within the boundary, the volume of organ within the slice;

(h) means for summing the local histograms corresponding to the various slices to obtain a global histogram indicative of the number of pixels within the organ boundaries of respective slices having each particular CT number;

(i) means for determining from the global histogram a demarcation CT number that distinguishes between normal organ tissue and tumor;

(j) means for determining from the volume computations for each of the slices, the total volume of the organ; and (k) means for computing from the global histogram and demarcation CT number, the volume of the tumor.

7. An arrangement according to claim 6 wherein said (d) means for generating comprises:

(1) means for operator specifying a CT number threshold criteria for defining the boundary of the organ;

(2) means for operator specifying a seed pixel by visually ascertaining an arbitrary point within the organ;

(3) means for searching from one pixel to the next, beginning at the seed pixel, to locate a first boundary pixel meeting the threshold criteria specified;

(4) means for examining nearest neighboring pixels to the first boundary pixel to determine if they meet the threshold criteria to find a second boundary pixel, (5) means for drawing a vector from the first boundary pixel to the second boundary pixel, (6) means for examining pixels neighboring to said second boundary pixel to determine third, fourth, . . . nth boundary pixels and drawing vectors from each last found pixel to a newly found pixel, to generate a series of vectors defining the boundary of the organ.

8. An arrangement according to claim 6 wherein said generating means comprises means for reading data defining the boundary determined for a previously boundary defined slice and utilizing that previously determined boundary for the current slice.

9. An arrangement according to claim 6 wherein said (j) means for determining comprises means for the operator to visually examine the global histogram and select the demarcation CT number based on predetermined criteria.

10. An arrangement according to claim 6 wherein said (j) means for determining comprises means for computer fitting the local histogram to a sum of three gaussian functions given by $$F(n) = \sum_{i=1}^{3} A_i \exp\left[ -\frac{(n - n_i)^2}{2\sigma_i^2} \right]. \quad (1)$$

wherein n represents the CT numbers and $n_i$ their mean value for each of the Gaussian functions, $A_i$ and $\sigma_i^2$ are the corresponding amplitude, and variance, respectively.

* * * * *